United States Patent
Macool et al.

(10) Patent No.: US 7,470,532 B2
(45) Date of Patent: Dec. 30, 2008

(54) _MORTIERELLA ALPINA_ $C_{16/18}$ FATTY ACID ELONGASE

(75) Inventors: Daniel Joseph Macool, Rutledge, PA (US); Zhixiong Xue, Chadds Ford, PA (US); Quinn Qun Zhu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/253,882

(22) Filed: Oct. 19, 2005

(65) Prior Publication Data

US 2007/0087420 A1 Apr. 19, 2007

(51) Int. Cl.
- C12N 1/20 (2006.01)
- C12N 9/10 (2006.01)
- C12N 1/21 (2006.01)
- C07H 21/04 (2006.01)
- C12P 7/64 (2006.01)

(52) U.S. Cl. .......... 435/252.3; 435/193; 435/69.1; 435/254.2; 435/254.1; 435/252.1; 435/255.2; 435/254.22; 435/257.1; 536/23.2

(58) Field of Classification Search .......... None
See application file for complete search history.

(56) References Cited

U.S. PATENT DOCUMENTS

| | | | |
|---|---|---|---|
| 6,075,183 | A | 6/2000 | Knutzon et al. |
| 6,677,145 | B2 | 1/2004 | Mukerji et al. |
| 2005/0089865 | A1 | 4/2005 | Napier et al. |
| 2005/0273895 | P1 | 12/2005 | Singh et al. |
| 2006/0048244 | A1 | 3/2006 | Mukerji et al. |
| 2006/0094087 | A1 | 5/2006 | Xue et al. |
| 2006/0094092 | A1* | 5/2006 | Damude et al. ............. 435/134 |

FOREIGN PATENT DOCUMENTS

JP 2008073030 A 4/2008

OTHER PUBLICATIONS

Shimizu, M. et al., M. alpina fatty acid chain elongation enzyme encoding sequence, SEQ ID 2, JP2008073030, GENA, Accession No. ARL18873, Apr. 3, 2008.
Astrid Meyer et al., Novel Fatty Acid Elongases and Their Use for the Reconsitution of Docosahexaenoic Acid Biosynthesis, Journal of LIPID Research, vol. 45:1899-1909, 2004.
Stuart Smith, The Animal Fatty Acid Synthase: One Gene, One Polypeptide, Seven Enzymes, FASEB J., vol. 8:1248-1259, 1994.
Amanda E. Leonard et al., Elongation of Long-Chain Fatty Acids, Progress in LIPID Research, vol. 43:36-54, 2004.
Suzette L. Pereira et al., Identification of Two Novel Microalgal Enzymes Involved in the Conversion of the W3-Fatty Acid, Eicosapentaenoic Acid, into Docosahexaenoic Acid, Biochem. J., vol. 364:357-366, 2004.
Marina Kniazeva et al., Suppression of the ELO-2 FA Elongation Activity Results in Alterations of the Fatty Acid Composition and Multiple Physiological Defects, Including Abnormal Ultradian Rhythms, in Caenorhabditis Elegans, Genetics, vol. 163:159-169, 2003.
National Center for Biotechnology Information General Identifier No. 46445240, Accession No: EAL04510, Aug. 6, 2004, T. Jones et al., The Diploid Genome Sequence of Candida Albicans.
National Center for Biotechnology Information General Identifier No. 85666116, Accession No: $NC_{13}$ 001142, Feb. 6, 2006, A. Goffeau et al., Life with 6000 Genes.

* cited by examiner

_Primary Examiner_—Rebecca Prouty
_Assistant Examiner_—Md. Younus Meah
(74) _Attorney, Agent, or Firm_—Neil Feltham; Loretta Smith

(57) ABSTRACT

The present invention relates to a fungal $C_{16/18}$ fatty acid elongase that is able to catalyze the conversion of palmitate (16:0) to stearic acid (18:0). Specifically, the nucleotide sequence of a _Mortierella alpina_ $C_{16/18}$ fatty acid elongase is provided (designated as "ELO3"). Methods of increasing microbial oil production, increasing carbon flux into the polyunsaturated fatty acid biosynthetic pathway and increasing the content of polyunsaturated fatty acids by over-expression of the $C_{16/18}$ fatty acid elongase are described herein. Most desirably, the substrate specificity of the instant ELO3 will be particularly useful to enable accumulation of long-chain polyunsaturated fatty acids in oleaginous yeast, such as _Yarrowia lipolytica_.

9 Claims, 3 Drawing Sheets

MORTIERELLA ALPINA $C_{16/18}$ FATTY ACID ELONGASE

FIELD OF THE INVENTION

Figure 1:
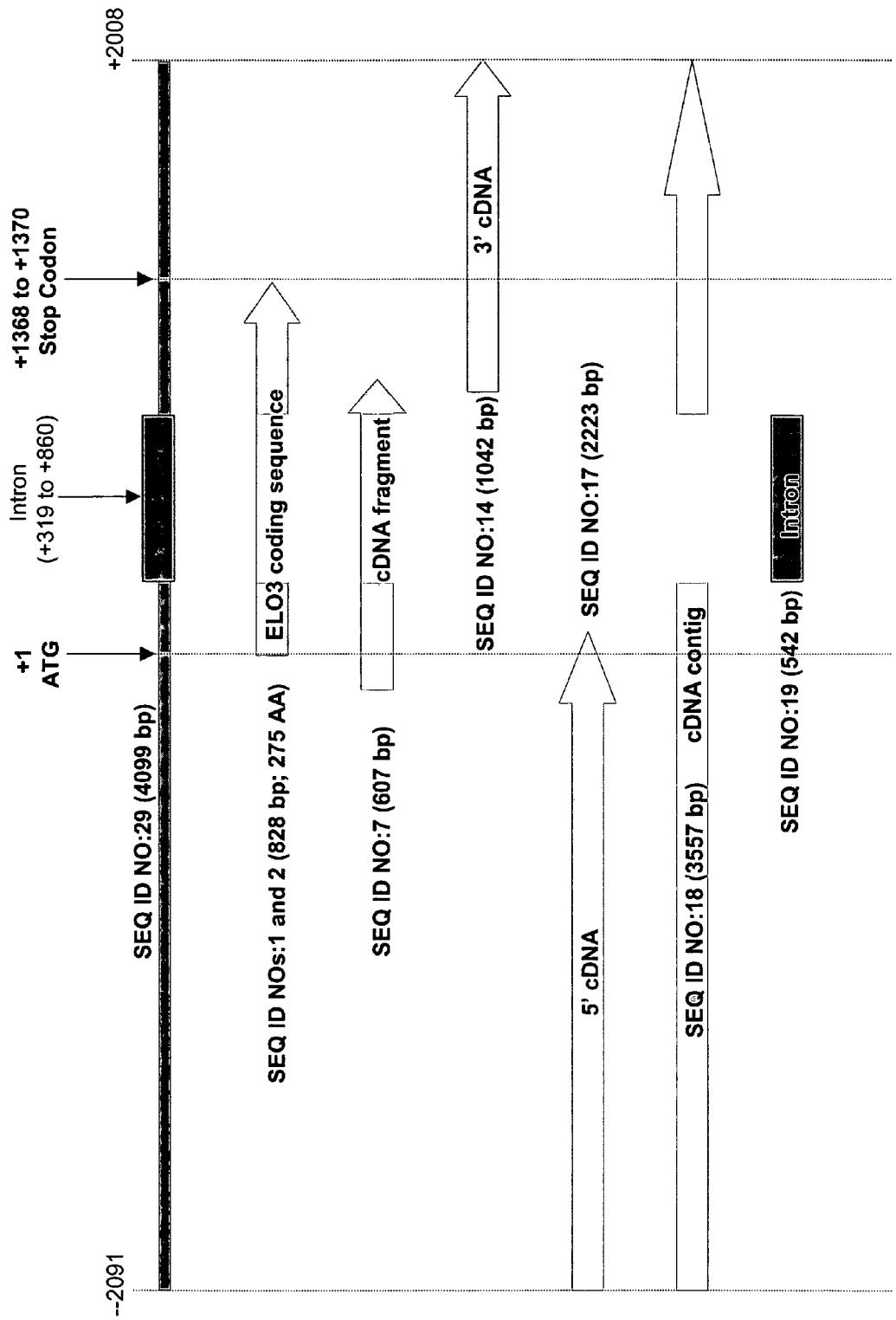

This invention is in the field of biotechnology. More specifically, this invention pertains to the isolation and characterization of a nucleic acid fragment encoding a $C_{16/18}$ fatty acid elongase enzyme useful for increasing the production of stearic acid in oleaginous microorganisms.

BACKGROUND OF THE INVENTION

Oil biosynthesis in a cell generically refers to the synthesis of triacylglycerols (TAGs), wherein TAGs are defined as neutral lipids consisting of three fatty acyl residues esterified to a glycerol molecule. Such oils can contain a wide spectrum of fatty acids, including saturated and unsaturated fatty acids and short-chain and long-chain fatty acids. And, not surprisingly, numerous factors affect the quantity of oil so produced and its final fatty acid composition within a specific microbe.

Although traditional approaches (e.g., breeding) and genetic engineering approaches have been successfully applied to produce oilseed plants that have improved oil content [demonstrated by the commercial availability of e.g., high-laurate canola, high-stearate canola, high-oleic soybean and high-oleic corn], similar manipulation of oil content in oleaginous microbes has not been significantly pursued in the past. Recent efforts to engineer microbes having the ability to commercially produce long-chain ω-3 and/or ω-6 polyunsaturated fatty acids ("PUFAs"; e.g., 18:3, 18:4, 20:3, 20:4, 20:5, 22:6 fatty acids) within their oil fraction, however, has created a need for methods to increase carbon flow into lipid metabolism.

Lipid metabolism in most organisms is catalyzed by a multi-enzyme fatty acid synthase complex ("FAS") and initially occurs by the condensation of eight two-carbon fragments (acetyl groups from acetyl-CoA) to form palmitate, a 16-carbon saturated fatty acid (Smith, S. *FASEB J.*, 8(15): 1248-59 (1994)). Once free palmitate (16:0) is released from FAS, the molecule undergoes either elongation (i.e., via a $C_{16/18}$ fatty acid elongase to produce stearic acid (18:0)) or unsaturation (i.e., via a Δ9 desaturase to produce palmitoleic acid (16:1)). All other fatty acid molecules are synthesized from these two metabolic precursors. Since the primary fate of palmitate is elongation, however (while desaturation is only a minor reaction in most organisms), it is concluded that $C_{16/18}$ fatty acid elongases play an important role in determining overall carbon flux into the fatty acid biosynthetic pathway, and thereby play a determinant role in both the quantity and composition of oil so produced.

A variety of fatty acid elongases have been isolated and characterized in recent years. For example, a useful review discussing the elongation of long-chain fatty acids in yeast, mammals, plants and lower eukaryotes is that of Leonard, A. E., et al. (*Prog. Lipid Res.* 43:36-54 (2004)). Table 1 of Leonard et al. provides a summary of fatty acid elongase genes, GenBank Accession Nos. and the reaction that each enzyme catalyzes (i.e., from *S. cerevisiae* [ELO1, ELO2, ELO3], human, mouse [Elov1, Elov2, Elov3, Elov4, Lce], rat [rELO1, rELO2], *Caenorhabditis elegans* [CEELO1], *Mortierella alpina* [GEELO, MAELO], *Isochrysis galbana* [IgASE1] and *Physcomitrella patens* [PSE1]). Additional fatty acid elongases that have been described and functionally characterized include those from: *Ostreococcus tauri* [OtELO1, OtELO2], *Thalassiosira pseudomana* [TpELO1, TpELO2], *Xenopus laevis* [XlELO] and *Oncorhynchus mykiss* [OmELO] (Meyer, A., et al., *J. Lipid Res.* 45(10): 1899-1909 (2004)); *Thraustochytrium aureum* (U.S. Pat. No. 6,677,145); *P. patens* [pavELO] (Pereira, S. et al., *Biochem. J.* 384:357-366 (2004)); and *Caenorhabditis elegans* CeELO2 (Kniazeva, M. et al., *Genetics* 163:159-169 (2003)). However, only the rat rELO2 and *C. elegans* CeELO2 elongases are classified as $C_{16/18}$ fatty acid elongases having the appropriate substrate specificity to enable conversion of palmitate to stearic acid. Thus, it was desirable herein to identify and characterize a novel $C_{16/18}$ fatty acid elongase as a means to permit the up-regulation of carbon flow into lipid metabolism in an oleaginous microbe using the techniques of genetic engineering.

Applicants have solved the stated problem by isolating the gene encoding a $C_{16/18}$ fatty acid elongase from *Mortierella alpina* and demonstrating increased conversion of 16:0 to 18:0 upon over-expression of the gene in the oleaginous yeast, *Yarrowia lipolytica*. This enabled increased PUFA content in the microbial oil and increased oil biosynthesis.

SUMMARY OF THE INVENTION

The invention relates to a gene encoding a $C_{16/18}$ fatty acid elongase enzyme isolated from *Mortierella* useful for the manipulation of the biochemical pathway leading to the production of microbial oils, and particularly in oleaginous yeast.

Accordingly the invention provides an isolated nucleic acid molecule encoding a $C_{16/18}$ fatty acid elongase enzyme, selected from the group consisting of:

(a) an isolated nucleic acid molecule encoding the amino acid sequence as set forth in SEQ ID NO:2;

(b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or, an isolated nucleic acid molecule that is completely complementary to (a) or (b).

Additionally the invention provides polypeptides encoded by the isolated nucleic acid molecules of the invention, genetic chimera and host cells expressing the same.

In a similar embodiment the invention provides an isolated nucleic acid molecule comprising a first nucleotide sequence encoding a $C_{16/18}$ fatty acid elongase enzyme of at least 275 amino acids that has at least 90% identity based on the BLAST method of alignment when compared to a polypeptide having the sequence as set forth in SEQ ID NO:2;

or a second nucleotide sequence comprising the complement of the first nucleotide sequence.

Additionally provided are methods for the production of stearic acid comprising:

a) providing an oleaginous yeast comprising an isolated nucleic acid fragment encoding a polypeptide having $C_{16/18}$ fatty acid elongase activity as set forth in SEQ ID NO:2 under the control of suitable regulatory sequences;

b) providing a source of elongase substrate comprising palmitate;

c) growing the oleaginous yeast of step (a) with the elongase substrate of (b) under conditions wherein the nucleic acid molecule of step (a)(i) or step (a)(ii) is expressed and stearic acid is produced; and, d) optionally recovering the stearic acid of step (c).

Similarly the invention provides A method for the production of polyunsaturated fatty acids comprising:

a) providing an oleaginous yeast comprising:
   (i) an isolated nucleic acid fragment encoding a polypeptide having $C_{16/18}$ fatty acid elongase activity as set forth in SEQ ID NO:2; and,
   (ii) genes encoding a functional polyunsaturated fatty acid biosynthetic pathway;
b) providing a source of elongase substrate comprising palmitate;
c) growing the oleaginous yeast of step (a) with the elongase substrate of (b) under conditions wherein polyunsaturated fatty acids are produced; and,
d) optionally recovering the polyunsaturated fatty acids of step (c).

In another embodiment the invention provides a microbial oil produced by the method of the invention.

BRIEF DESCRIPTION OF THE DRAWINGS AND SEQUENCE DESCRIPTIONS

FIG. 1 graphically represents the relationship between SEQ ID NOs:1, 2, 7, 14, 17, 18, 19 and 29, each of which relates to the $C_{16/18}$ fatty acid elongase enzyme (ELO3) in *Mortierella alpina*.

Figure 2:
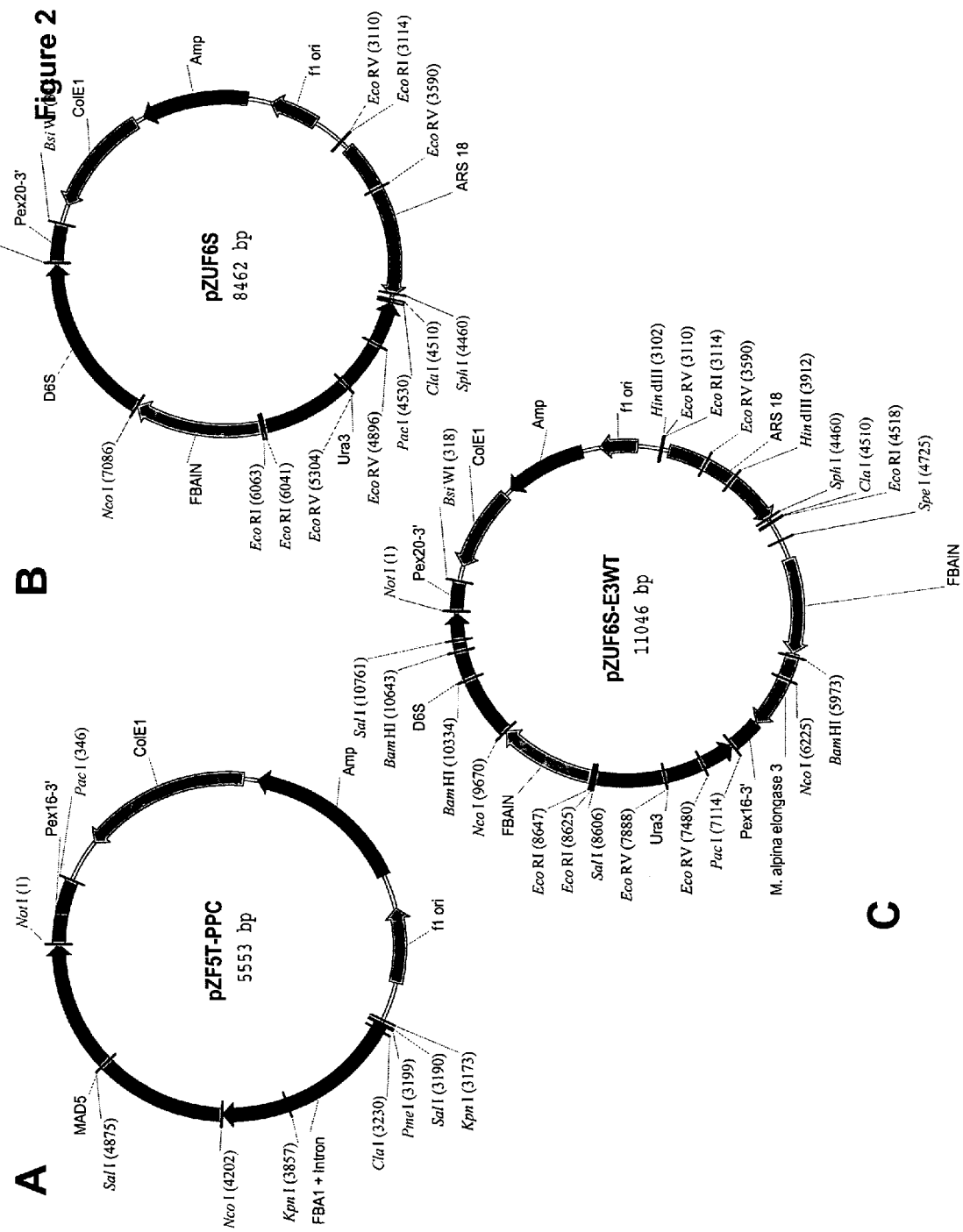

FIG. 2 provides plasmid maps for the following: (A) pZF5T-PPC; (B) pZUF6S; and (C) pZUF6S-E3WT.

Figure 3:
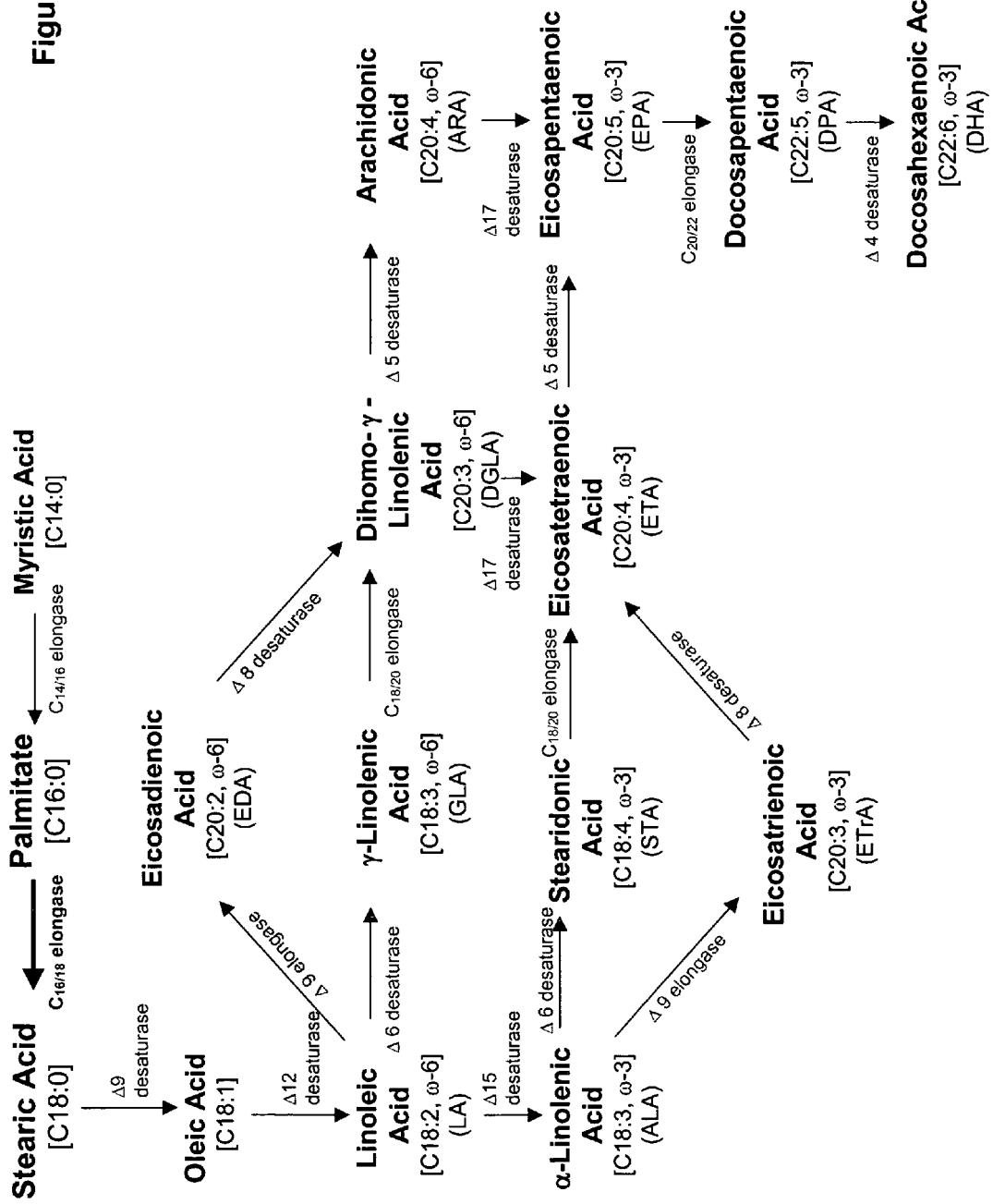

FIG. 3 illustrates the PUFA biosynthetic pathway and precursors.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1, 2, 7, 14, 17-22 and 25-28 are ORFs encoding genes or proteins (or portions thereof) or plasmids, as identified in Table 1.

TABLE 1

Summary Of Gene And Protein SEQ ID Numbers

| Description | ORF Nucleic acid SEQ ID NO. | Protein SEQ ID NO. |
|---|---|---|
| *Mortierella alpina* $C_{16/18}$ fatty acid elongase (ELO3)-coding region | 1 (828 bp) | 2 (275 AA) |
| *Mortierella alpina* ELO3-partial cDNA sequence | 7 (607 bp) | — |
| *Mortierella alpina* ELO3-3' sequence obtained by genome walking | 14 (1,042 bp) | — |
| *Mortierella alpina* ELO3-5' sequence obtained by genome walking | 17 (2,223 bp) | — |
| *Mortierella alpina* ELO3-cDNA contig | 18 (3,557 bp) | — |
| *Mortierella alpina* ELO3-intron | 19 (542 bp) | — |
| *Mortierella alpina* ELO3-genomic contig | 29 (4,099 bp) | — |
| Plasmid pKUNT2 | 20 (6,457 bp) | — |
| *Yarrowia lipolytica* Δ12 desaturase | 21 (1,936 bp) | 22 (419 AA) |
| Plasmid pZF5T-PPC | 25 (5,553 bp) | — |
| Plasmid pZF5T-PPC-E3 | 26 (5,031 bp) | — |
| Plasmid pZUF6S | 27 (8,462 bp) | — |
| Plasmid pZUF6S-E3WT | 28 (11,046 bp) | — |

SEQ ID NOs:3, 4 and 5 correspond to BD-Clontech Creator Smart® cDNA library kit primers SMART IV oligonucleotide, CDSIII/3' PCR primer and 5'-PCR primer.

SEQ ID NO:6 corresponds to the M13 forward primer used for cDNA library sequencing.

SEQ ID NOs:8 and 9 correspond to the Genome Walker adaptor from ClonTech's Universal GenomeWalker™ Kit, used for genome-walking to isolate the 3'-end region of the *M. alpina* ELO3.

SEQ ID NOs:10-13 correspond to primers MA Elong 3'1, AP1, MA elong 3'2 and AP2, respectively, used for genome-walking to isolate the 3'-end region of the *M. alpina* ELO3.

SEQ ID NOs:15 and 16 correspond to primers MA Elong 5'1 and MA Elong 5'2, respectively, used for genome-walking to isolate the 5'-end region of the *M. alpina* ELO3.

SEQ ID NOs:23 and 24 correspond to primers MA ELONG 5' NcoI 3 and MA ELONG 3' NotI 1, respectively, used for amplifying the complete ELO3 from *M. alpina* cDNA.

DETAILED DESCRIPTION OF THE INVENTION

All patents, patent applications, and publications cited herein are incorporated by reference in their entirety. This specifically includes, but is not limited to, the following Applicants' Assignee's copending applications: U.S. patent application Ser. No. 10/840478 (filed May 6, 2004), U.S. patent application Ser. No. 10/840579 (filed May 6, 2004), U.S. patent application Ser. No. 10/869630 (filed Jun. 16, 2004), U.S. patent application Ser. No. 10/987548 (filed Nov. 12, 2004), U.S. patent application Ser. No. 11/225354 (filed Sep. 13, 2005), U.S. Patent Application Ser.No. 60/624812 (filed Nov. 4, 2004), U.S. patent application Ser. No. 11/183664 (filed Jul. 18, 2005) and U.S. patent application Ser. No. 11/185301 (filed Jul. 20, 2005).

Applicants have isolated a Mortierella alpina gene encoding a $C_{16/18}$ fatty acid elongase, which is responsible for the conversion of palmitate to stearic acid. This gene (identified herein as "ELO3") may be useful to alter the quantity of long-chain polyunsaturated fatty acids (PUFAs) produced in oleaginous yeast, such as *Yarrowia lipolytica*.

The importance of PUFAs are undisputed. For example, certain PUFAs are important biological components of healthy cells and are recognized as "essential" fatty acids that cannot be synthesized de novo in mammals and instead must be obtained either in the diet or derived by further desaturation and elongation of linoleic acid (LA) or α-linolenic acid (ALA). Additionally, a high intake of long-chain ω-3 PUFAs produces cardiovascular protective effects (Dyerberg, J. et al., *Amer. J. Clin Nutr.* 28:958-966 (1975); Dyerberg, J. et al., *Lancet* 2(8081):117-119 (Jul. 15, 1978); Shimokawa, H.,

*World Rev Nutr Diet,* 88:100-108 (2001); von Schacky, C., and Dyerberg, J., *World Rev Nutr Diet,* 88:90-99 (2001)). Numerous other studies document wide-ranging health benefits conferred by administration of ω-3 and/or ω-6 fatty acids against a variety of symptoms and diseases (e.g., asthma, psoriasis, eczema, diabetes, cancer).

As such, the subject invention finds many applications. PUFAs, or derivatives thereof, accumulated by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with ARA can result not only in increased levels of ARA, but also downstream products of ARA such as prostaglandins. Complex regulatory mechanisms can make it desirable to combine various PUFAs, or add different conjugates of PUFAs, in order to prevent, control or overcome such mechanisms to achieve the desired levels of specific PUFAs in an individual.

DEFINITIONS

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Microbial oils" or "single cell oils" are those oils naturally produced by microorganisms (e.g., algae, oleaginous yeasts and filamentous fungi) during their lifespan. These oils are generally stored in the cell as "neutral lipids". The terms "triacylglycerol", "oil" and "TAGs" refer to neutral lipids composed of three fatty acyl residues esterified to a glycerol molecule (and such terms will be used interchangeably throughout the present disclosure herein). Such oils can contain short and long chain saturated and unsaturated fatty acids. Thus, "oil biosynthesis" generically refers to the synthesis of TAGs in the cell.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" ((ω-6 or n-6) versus "omega-3 fatty acids" (ω-3 or n-3) are provided in WO2004/101757.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the specification and each compounds' chemical name.

TABLE 2

Nomenclature Of Some Fatty Acids

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linolenic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosa-tetraenoic | ETA | cis-8,11,14,17-eicosatetraenoic | 20:4 ω-3 |
| Eicosa-pentaenoic | EPA | cis-5,8,11,14,17-eicosapentaenoic | 20:5 ω-3 |
| Docosa-pentaenoic | DPA | cis-7,10,13,16,19-docosapentaenoic | 22:5 ω-3 |
| Docosa-hexaenoic | DHA | cis-4,7,10,13,16,19-docosahexaenoic | 22:6 ω-3 |

An "elongase system" refers to suite of four enzymes that are responsible for elongation of a fatty acid carbon chain to produce an acid that is 2 carbons longer than the fatty acid substrate that the elongase system acts upon. More specifically, the process of elongation occurs in association with fatty acid synthase, whereby CoA is the acyl carrier (Lassner et al., *The Plant Cell* 8:281-292 (1996)). In the first step, which has been found to be both substrate-specific and also rate-limiting, malonyl-CoA is condensed with a long-chain acyl-CoA to yield $CO_2$ and a β-ketoacyl-CoA (where the acyl moiety has been elongated by two carbon atoms). For the purposes herein, an enzyme catalyzing this first condensation reaction will be referred to hereinafter as an "elongase" or a "fatty acid elongase". Subsequent reactions include reduction to β-hydroxyacyl-CoA, dehydration to an enoyl-CoA, and a second reduction to yield the elongated acyl-CoA.

As is well known in the art, fatty acid elongases can have different substrate specificities and selectivities, wherein "substrate specificities" refers to the activity of the enzyme when faced with a single substrate and "substrate selectivity" describes the selection of a particular substrate from a substrate mixture. For example, a $C_{16/18}$ fatty acid elongase will prefer a $C_{16}$ substrate, a $C_{18/20}$ fatty acid elongase will prefer a $C_{18}$ substrate and a $C_{20/22}$ fatty acid elongase will prefer a $C_{20}$ substrate. In like manner, a Δ9 fatty acid elongase is able to catalyze the conversion of LA and ALA to EDA and ETrA, respectively. It is important to note that some fatty acid elongases have broad specificity and thus a single enzyme may be capable of catalyzing several fatty acid elongase reactions (e.g., thereby acting as both a $C_{16/18}$ fatty acid elongase and a $C_{18/20}$ fatty acid elongase). In preferred embodiments, it is most desirable to empirically determine the specificity of a fatty acid elongase by transforming a suitable host with the gene for the fatty acid elongase and determining its effect on the fatty acid profile of the host.

Within the context of the present disclosure, the term "ELO3" refers to a *Mortierella alpina* $C_{16/18}$ fatty acid elongase enzyme (provided herein as SEQ ID NO:2), encoded by the elo3 gene (SEQ ID NO:1). Based on data reported herein, ELO3 preferentially catalyzes the conversion of palmitate (16:0) to stearic acid (18:0).

The term "desaturase" refers to a polypeptide that can desaturate, i.e., introduce a double bond, in one or more fatty acids to produce a mono- or polyunsaturated fatty acid. Despite use of the omega-reference system throughout the specification in reference to specific fatty acids, it is more convenient to indicate the activity of a desaturase by counting from the carboxyl end of the substrate using the delta-system. Of particular interest herein are Δ9 desaturases that catalyze the conversion of palmitate to palmitoleic acid (16:1) and/or stearate to oleic acid (18:1). Other desaturases relevant to the present disclosure include: Δ12 desaturases that desaturate a fatty acid between the $12^{th}$ and $13^{th}$ carbon atoms numbered from the carboxyl-terminal end of the molecule and that catalyze the conversion of oleic acid to LA; Δ15 desaturases that catalyze the conversion of LA to ALA; Δ17 desaturases that catalyze the conversion of DGLA to ETA and/or ARA to EPA; Δ6 desaturases that catalyze the conversion of LA to GLA and/or ALA to STA; Δ5 desaturases that catalyze the conversion of DGLA to ARA and/or ETA to EPA; Δ4 desaturases that catalyze the conversion of DPA to DHA; and, Δ8 desaturases that catalyze the conversion of EDA to DGLA and/or ETrA to ETA.

The terms "conversion efficiency" and "percent substrate conversion" refer to the efficiency by which a particular enzyme (e.g., a desaturase or elongase) can convert substrate to product. The conversion efficiency is measured according to the following formula: ([product]/[substrate+product]) *100, where 'product' includes the immediate product and all products in the pathway derived from it.

The term "PUFA biosynthetic pathway enzyme" refers to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase, a Δ9 fatty acid elongase, a $C_{14/16}$ fatty acid elongase, a $C_{16/18}$ fatty acid elongase, a $C_{18/20}$ fatty acid elongase and/or a $C_{20/22}$ fatty acid elongase. Similarly, the term "ω-3/ω-6 fatty acid biosynthetic pathway" refers to a set of genes which, when expressed under the appropriate conditions encode enzymes that catalyze the direct or indirect production of either or both ω-3 and ω-6 fatty acids. A representative pathway is illustrated in FIG. 3, providing for the conversion of myristic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "functional" as used herein in context with the PUFA biosynthetic pathway means that some (or all of) the genes in the pathway express active enzymes. It should be understood that "PUFA biosynthetic pathway" or "functional PUFA biosynthetic pathway" does not imply that all the genes listed in the above paragraph are required, as a number of fatty acid products will only require the expression of a subset of the genes of this pathway.

The term "oleaginous" refers to those organisms that tend to store their energy source in the form of lipid (Weete, In: Fungal Lipid Biochemistry, $2^{nd}$ ed., Plenum, 1980). The term "oleaginous yeast" refers to those microorganisms classified as yeasts that can make oil. Generally, the cellular oil or TAG content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

As used herein, the terms "isolated nucleic acid fragment" or "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual, $2^{nd}$* ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: N.J. (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences-tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS.* 5:151-153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc., Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.,* [Proc. Int. Symp.] (1994), Meeting Date 1992, 111-20. Suhai, Sandor, Ed. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon optimized" as it refers to genes or coding regions of nucleic acid fragments, refers to the alteration of codons in the gene or coding regions of the nucleic acid molecules to reflect the typical codon usage of the host organism without altering the polypeptide for which the DNA codes.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment(s) of the invention. Expression may also refer to translation of mRNA into a polypeptide.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene(s) and having elements in addition to the foreign gene(s) that allow for enhanced expression of that gene in a foreign host.

The term "homologous recombination" refers to the exchange of DNA fragments between two DNA molecules (during cross over). The fragments that are exchanged are flanked by sites of identical nucleotide sequences between the two DNA molecules (i.e., "regions of homology").

The term "regions of homology" refer to stretches of nucleotide sequence on nucleic acid fragments that participate in homologous recombination that have homology to each other. Effective homologous recombination will generally take place where these regions of homology are at least about 10 bp in length where at least about 50 bp in length is preferred. Typically fragments that are intended for recombination contain at least two regions of homology where targeted gene disruption or replacement is desired.

Standard recombinant DNA and molecular cloning techniques used herein are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987). Sequence Identification Of The *Mortierella alpina* $C_{16/18}$ Fatt Acid Elongase In the present invention, a gene encoding a $C_{16/18}$ fatty acid elongase (designated herein as "ELO3") has been isolated from a proprietary DuPont cDNA library of *Mortierella alpina*. *M. alpina* is an organism that naturally accumulates fatty acids having chain lengths equal to or greater than $C_{20}$ in its TAG fraction, thus indicating that the $C_{16/18}$ fatty acid elongase likely functions with high efficiency to ensure a large flow of stearic acid into the PUFA biosynthetic pathway.

Comparison of the $C_{16/18}$ fatty acid elongase nucleotide base and deduced amino acid sequences to public databases, using a BLAST algorithm (Altschul, S. F., et al., *Nucleic Acids Res.* 25:3389-3402 (1997)), reveals that the most similar known sequences are about 37% identical to the amino acid sequence of the $C_{16/18}$ fatty acid elongase reported herein over a length of 275 amino acids. Preferred amino acid fragments are at least about 70%-80% identical to the sequences herein, where those sequences that are 85%-90% identical are particularly suitable and those sequences that are about 95% identical are most preferred. Similarly, preferred $C_{16/18}$ fatty acid elongase encoding nucleic acid sequences corresponding to the instant ORF are those encoding active proteins and which are at least about 70%-80% identical to the nucleic acid sequences encoding $C_{16/18}$ fatty acid elongase reported herein, where those sequences that are 85%-90% identical are particularly suitable and those sequences that are about 95% identical are most preferred.

Identification and Isolation of Homologs

The $C_{16/18}$ fatty acid elongase nucleic acid fragment of the instant invention may be used to identify and isolate genes encoding homologous proteins from the same or other bacterial, algal, fungal or plant species.

Identification Techniques: For example, a substantial portion of the *Mortierella alpina* $C_{16/18}$ fatty acid elongase amino acid or nucleotide sequence described herein can be used to putatively identify related polypeptides or genes, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)) and ClustalW (Megalign program of DNASTAR software).

Alternatively, the instant fatty acid elongase sequence may be employed as a hybridization reagent for the identification of homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Isolation Methods: The Mortierella alpina $C_{16/18}$ fatty acid elongase identified herein may be used to isolate genes encoding homologous proteins from the same or other bacterial, algal, fungal or plant species, based on sequence-dependent protocols. For example, these protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, genes encoding similar proteins or polypeptides to the fatty acid elongase described herein could be isolated directly by using all or a portion of the instant nucleic acid fragments as DNA hybridization probes to screen libraries from any desired yeast or fungus using methodology well known to those skilled in the art (wherein those yeast or fungus producing PUFAs would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, V A; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant ELO3 sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Or, the second primer sequence may be based upon sequences derived from the cloning vector, e.g., using the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *PNAS USA* 86:5673 (1989); Loh et al., *Science* 243:217 (1989)).

Availability of the instant nucleotide and deduced amino acid $C_{16/18}$ fatty acid elongase sequences facilitates immunological screening of DNA expression libraries. Synthetic peptides representing portions of the instant amino acid sequence may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A. *Adv. Immunol.* 36:1 (1984); Maniatis, supra).

Gene Optimization for Improved Heterologous Expression

Following the identification and isolation of a particular $C_{16/18}$ fatty acid elongase (e.g., SEQ ID NOs:1 and 2), a variety of techniques can be utilized to improve expression of the $C_{16/18}$ fatty acid elongase of interest in an alternative host. Two such techniques include codon-optimization and mutagenesis of the gene.

As will be appreciated by one skilled in the art, it is frequently useful to modify a portion of the codons encoding a particular polypeptide that is to be expressed in a foreign host (such that the modified polypeptide uses codons that are preferred by the alternate host) since this can substantially enhance the expression of the foreign gene encoding the polypeptide. One skilled in the art will be familiar with the techniques for determining the host preferred codons within a particular host species of interest and calculating and synthesizing the alternate coding sequence (e.g., see WO2004/101753). Thus, for example, in one embodiment of the invention, it may be desirable to modify a portion of the codons encoding the ELO3 polypeptide to enhance the expression of the gene in *Yarrowia lipolytica*.

In alternate embodiments, mutagenesis techniques such as in vitro mutagenesis and selection, site-directed mutagenesis, error prone PCR (Melnikov et al., *Nucleic Acids Research*, 27(4):1056-1062 (Feb. 15, 1999)), "gene shuffling" (U.S. Pat. No. 5,605,793; U.S. Pat. No. 5,811,238; U.S. Pat. No. 5,830,721; and U.S. Pat. No. 5,837,458) or other means can be employed to obtain mutations of naturally occurring elongase genes, such as the $C_{16/18}$ fatty acid elongase described herein (wherein such mutations may include deletions, insertions and point mutations, or combinations thereof). This would permit production of a polypeptide having fatty acid elongase activity in vivo with more desirable physical and kinetic parameters for function in a particular host cell (e.g., a longer half-life or a higher rate of production of a desired fatty acid). Or, if desired, the regions of a polypeptide of interest important for enzymatic activity can be determined through routine mutagenesis, expression of the resulting mutant polypeptides and determination of their activities. An overview of these techniques are described in WO 2004/101757.

All such mutant proteins and nucleotide sequences encoding them that are derived from the $C_{16/18}$ fatty acid elongase gene described herein are within the scope of the present invention. And, the methodologies of the present invention comprise use of the complete sequence of the $C_{16/18}$ fatty acid elongase gene as reported in the accompanying Sequence Listing, the complement of this complete sequence, substantial portions of this sequence, codon-optimized elongases derived therefrom, and those sequences that are substantially homologous thereto.

Microbial Biosynthesis of Fatty Acids

Lipid metabolism is a basic metabolic process that almost all animals, plants, and microorganisms possess; and thus, almost all of these organisms possess the ability to synthesize palmitate (16:0), stearic acid (18:0) and oleic acid (18:1) (since these fatty acids are essential for phospholipid biosynthesis). As illustrated in FIG. 3, each of these fatty acids is derived from myristic acid (14:0). Specifically, free palmitate is produced from myristic acid via an elongation reaction (i.e., catalyzed by a $C_{14/16}$ fatty acid elongase); subsequently, palmitate can be elongated by a $C_{16/18}$ fatty acid elongase to produce stearic acid or unsaturated to produce palmitoleic acid (16:1)). Since the primary fate of palmitate is elongation, however, it is concluded that $C_{16/18}$ fatty acid elongases play an important role in determining overall carbon flux into the fatty acid biosynthetic pathway since these enzymes control the amount of stearic acid produced in the microbial cell.

Methods useful for manipulating biochemical pathways are well known to those skilled in the art. It is expected that introduction of chimeric genes encoding the $C_{16/18}$ fatty acid elongase described herein, under the control of the appropriate promoters will result in increased production of stearic acid in a transformed host organism. As such, it is an object of the present invention to provide a method for the production of stearic acid in an oleaginous yeast, wherein the oleaginous yeast is provided: (a) an isolated nucleic acid fragment encoding a $C_{16/18}$ fatty acid elongase as set forth in SEQ ID NO:2; and, (b) a source of elongase substrate comprising palmitate; wherein the yeast is grown under conditions such that the chimeric elongase gene is expressed and the palmitate is converted to stearic acid, and wherein the stearic acid is optionally recovered.

Furthermore, the $C_{16/18}$ fatty acid elongase gene and its corresponding enzyme product described herein can be used indirectly for the production of ω-3 and/or ω-6 PUFAs. Specifically, it is contemplated that the $C_{16/18}$ fatty acid elongase described herein may be expressed in conjunction with one or more genes that encode other enzymes, such that a series of reactions occur to produce a desired PUFA product.

Although many microorganisms (including algae, bacteria, molds, fungi and yeast) can synthesize PUFAs and omega fatty acids in the ordinary course of cellular metabolism, it is also possible to introduce this capability into an organism that does not natively produce PUFAs (or produce the desired PUFAs and/or lipid profile). One skilled in the art will be familiar with the considerations and techniques necessary to introduce an expression cassette(s) encoding appropriate enzymes for PUFA biosynthesis into the host organism of choice. For these purposes, a variety of desaturase and elongase genes involved in PUFA production have been identified through genetic means and the DNA sequences of some of these genes are publicly available (e.g., see WO 2004/101757 for a review of available genes in GenBank and/or the patent literature and considerations for choosing a specific polypeptide having desaturase or elongase activity). And, although not elaborated in detail herein, numerous teachings are provided in the literature wherein various organisms are engineered to produce specific PUFAs; some illustrative references are provided as follows, although these should not be construed as limiting: WO 98/46763; WO 98/46764; WO 98/46765; WO 99/64616; WO 2002/077213; WO 2003/093482; WO 2004/057001; WO 2004/090123; WO 2004/087902; U.S. Pat. No. 6,140,486; U.S. Pat No.6,459,018; U.S. Pat. No. 6,136,574; U.S. 2003/0172399; U.S. 2004/0172682; U.S. 2004/098762; U.S. 2004/0111763; U.S. 2004/0053379; U.S. 2004/0049805; U.S. 2004/0237139; U.S. 04/0172682; Beaudoin F. et al., *PNAS USA,* 97(12):6421-6426 (2000); Dyer, J. M. et al., *Appl. Envi. Microbiol.,* 59:224-230 (2002); Domergue, F. et al. *Eur. J. Biochem.* 269:4105-4113 (2002); Qi, B. et al., *Nature Biotech.* 22:739-745 (2004); and Abbadi et al., *The Plant Cell,* 16:2734-2748 (2004)).

Thus, for example, the $C_{16/18}$ fatty acid elongase described herein may be expressed in conjunction with one or more PUFA biosynthetic pathway genes that encode PUFA enzymes, such that a series of reactions occur to produce a desired PUFA product. In a preferred embodiment, for example, a host organism may be co-transformed with: 1.) a chimeric gene encoding the *M. alpina* $C_{16/18}$ fatty acid elongase of the present invention; and, 2.) a vector comprising additional genes encoding enzymes of the PUFA biosynthetic pathway (e.g., Δ9 desaturase, Δ12 desaturase, Δ6 desaturase, $C_{18/20}$ fatty acid elongase, Δ5 desaturase, Δ17 desaturase, $C_{20/22}$ fatty acid elongase, Δ4 desaturase, Δ15 desaturase, Δ9 fatty acid elongase and/or Δ8 desaturase). This transformant host would be expected to produce increased quantities of ω-3 and/or ω-6 fatty acids (e.g., LA, ALA, EDA, GLA, STA, ETrA, DGLA, ETA, ARA, EPA, DPA and DHA; see FIG. 3), than would occur in the same transformant host that was not expressing a chimeric gene encoding the *M. alpina* $C_{16/18}$ fatty acid elongase of the present invention. The particular genes included within a particular expression cassette will depend on the host cell (and its PUFA profile and/or desaturase/elongase profile), the availability of substrate, and the desired end product(s).

In alternative embodiments, it may be useful to disrupt a host organism's native $C_{16/18}$ fatty acid elongase, based on the complete sequences described herein, the complement of those complete sequences, substantial portions of those sequences, codon-optimized desaturases derived therefrom and those sequences that are substantially homologous thereto. For example, the targeted disruption of the $C_{16/18}$ fatty acid elongase in a host organism produces a mutant strain that is unable to synthesize stearic acid, thus requiring supplementation of C18 fatty acids for survival.

In an alternate embodiment, a transformant host organism comprising a disruption or inactivation of its native $C_{16/18}$ fatty acid elongase may then be advantageously transformed to express a heterologous $C_{16/18}$ fatty acid elongase (e.g., if the heterologous $C_{16/18}$ fatty acid elongase has different substrate specificity than the native $C_{16/18}$ fatty acid elongase). This manipulation could reduce substrate competition between the native and heterologous $C_{16/18}$ fatty acid elongase. Thus, expression of a heterologous $C_{16/18}$ fatty acid elongase (i.e. SEQ ID NO:2) in conjunction with a knockout of the corresponding native *Yarrowia lipolytica* $C_{16/18}$ fatty acid elongase could significantly increase the overall long-chain ω-3/ω-6 PUFAs that are produced in transformant *Y. lipolytica* host cells engineered for PUFA biosynthesis.

For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al., *J. Bacteriol.* 171:4617-4622 (1989); Balbas et al., *Gene* 136:211-213 (1993); Gueldener et al., *Nucleic Acids Res.* 24:2519-2524 (1996); and Smith et al., *Methods Mol. Cell. Biol.* 5:270-277(1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based (e.g., mutagenesis via UV radiation/chemical agents or use of transposable elements/transposons; see U.S. Ser. No. 10/840579).

Expression Systems, Cassettes and Vectors

The gene and gene product of the instant sequences described herein may be produced in heterologous microbial host cells, particularly in the cells of oleaginous yeast (e.g., *Yarrowia lipolytica*).

Microbial expression systems and expression vectors containing regulatory sequences that direct high level expression of foreign proteins are well known to those skilled in the art. Any of these could be used to construct chimeric genes for production of the gene product of the instant fatty acid elongase sequence. These chimeric genes could then be introduced into appropriate microorganisms via transformation to provide high-level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host (see e.g., U.S. Ser. No. 10/840579 for a review of useful initiation control regions and terminators). In some preferred embodiments, however, the transcriptional initiation regulatory regions are obtained from: glyceraldehyde-3-phosphate-dehydrogenase (U.S. Ser. No. 10/869630; co-pending U.S. patent application Ser. No. 11/183664), phosphoglycerate mutase (U.S. Ser. No. 10/869630), fructose-bisphosphate aldolase (U.S. Ser. No. 10/987548), glycerol-3-phosphate O-acyltransferase (U.S. Patent Application No. 60/610060), ammonium transporter proteins (co-pending U.S. patent application Ser. No. 11/185301) and the translation elongation factor EF1-α (TEF) protein (U.S. Pat. No. 6,265,185).

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of the $C_{16/18}$ fatty acid elongase described herein.

Preferred Microbial Hosts for Recombinant Expression of $C_{16/18}$ Fatty Acid Elongases Host cells for expression of the instant $C_{16/18}$ fatty acid elongase gene and nucleic acid fragments may include microbial hosts that grow on a variety of feedstocks, including simple or complex carbohydrates, organic acids and alcohols and/or hydrocarbons over a wide range of temperature and pH values. Although the gene described in the instant invention has been isolated for expression in an oleaginous yeast, and in particular *Yarrowia lipolytica*, it is contemplated that because transcription, translation and the protein biosynthetic apparatus is highly conserved, any bacteria, yeast, algae and/or filamentous fungus will be a suitable host for expression of the present nucleic acid fragments.

Preferred microbial hosts are oleaginous organisms, such as oleaginous yeast. These oleaginous organisms are naturally capable of oil synthesis and accumulation, wherein the total oil content can comprise greater than about 25% of the cellular dry weight, more preferably greater than about 30% of the cellular dry weight and most preferably greater than about 40% of the cellular dry weight. Additionally, there is basis for the use of these organisms for the production of PUFAs, as seen in U.S. Ser. No. 10/840579 and co-pending U.S. Patent Application No. 60/624812.

Genera typically identified as oleaginous yeast include, but are not limited to: *Yarrowia*, *Candida*, *Rhodotorula*, *Rhodosporidium*, *Cryptococcus*, *Trichosporon* and *Lipomyces*. More specifically, illustrative oil-synthesizing yeast include: *Rhodosporidium toruloides*, *Lipomyces starkeyii*, *L. lipoferus*, *Candida revkaufi*, *C. pulcherrima*, *C. tropicalis*, *C. utilis*, *Trichosporon pullans*, *T. cutaneum*, *Rhodotorula glutinus*, *R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982, ATCC #90812 and/or LGAM S(7)1 (Papanikolaou S., and Aggelis G., *Bioresour. Technol.* 82(1): 43-9 (2002)).

Transformation of Microbial Hosts

Once the DNA encoding a polypeptide suitable for expression in an oleaginous yeast has been obtained, it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the $C_{16/18}$ fatty acid elongase gene of interest may be introduced into a host cell by any standard technique. These techniques include transformation (e.g., lithium acetate transformation [*Methods in Enzymology*, 194: 186-187 (1991)]), protoplast fusion, biolistic impact, electroporation, microinjection, or any other method that introduces the gene of interest into the host cell. More specific teachings applicable for oleaginous yeast (i.e., *Yarrowia lipolytica*) include U.S. Pat. No. 4,880,741 and No. 5,071,764 and Chen, D. C. et al. (*Appl Microbiol Biotechnol.* 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by various selection techniques, as described in U.S. Ser. No. 10/840579 and U.S. Ser. No. 10/869630. Some preferred selection methods for use herein are resistance to kanamycin, hygromycin and the amino glycoside G418, as well as ability to grow on media lacking uracil, leucine, lysine, tryptophan or histidine.

Following transformation, substrates suitable for the instant $C_{16/18}$ fatty acid elongase (and, optionally other PUFA enzymes that are co-expressed within the host cell) may be produced by the host either naturally or transgenically, or they may be provided exogenously.

Fermentation Processes for Stearic Acid Production

The transformed microbial host cell is grown under conditions that optimize activity of fatty acid biosynthetic genes and produce the greatest and the most economical yield of fatty acids (e.g., stearic acid, which can in turn increase the production of various ω-3 and/or ω-6 fatty acids). In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose or sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Furthermore, the carbon substrate may include one-carbon substrates (e.g., carbon dioxide or methanol) for which metabolic conversion into key biochemical intermediates has been demonstrated. Hence it is contemplated that the source of carbon utilized in the present invention may encompass a wide variety of carbon-containing substrates and will only be limited by the choice of the host organism. Although all of the above mentioned carbon substrates and mixtures thereof are expected to be suitable in the present invention, preferred carbon substrates are sugars and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins, and other components known to those skilled in the art, suitable for the growth of the microorganism and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. This approach is described in WO 2004/101757, as are various suitable fermentation process designs (i.e., batch, fed-batch and continuous) and considerations during growth.

Purification Of PUFAs

Fatty acids, including PUFAs, may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-491 (1992)). A brief review of downstream processing is also available by A. Singh and O. Ward (*Adv. Appl. Microbiol.* 45:271-312 (1997)).

In general, means for the purification of PUFAs may include extraction with organic solvents, sonication, super-critical fluid extraction (e.g., using carbon dioxide), saponification, and physical means such as presses, or combinations thereof. One is referred to the teachings of WO 2004/101757 for additional details.

DESCRIPTION OF PREFERRED EMBODIMENTS

The ultimate goal of the work described herein is the development of an oleaginous yeast that accumulates oils enriched in ω-3 and/or ω-6 PUFAs. Toward this end, fatty acid elongases must be identified that function efficiently in oleaginous yeast, to enable synthesis and high accumulation of preferred PUFAs in these hosts. In previous work, the Applicants overexpressed a rat $C_{16/18}$ fatty acid elongase protein (rELO2 from *Rattus norvegicus*; GenBank Accession No. AB071986); and, although rELO2 was successfully expressed in *Yarrowia lipolytica* as a means to increase the production of down-stream PUFAs (U.S. Patent Application No. 60/624812), the presence of this gene in the transformed host was not conducive toward the acquisition of regulatory approvals. As a result, the present work was undertaken to identify a more suitable $C_{16/18}$ fatty acid elongase.

A cDNA fragment was identified in a proprietary *Mortierella alpina* cDNA library, based on BLAST analyses. The coding region of the gene (tentatively named "elo3") was over-expressed in *Yarrowia lipolytica* under the control of a strong native promoter, thereby resulting in transformants that produced 35% more C18 fatty acids (18:0, C18:1, C18:2 and GLA) and 31% less C16 fatty acids than the control strains. Thus, these data demonstrated that the *M. alpina* ELO3 uses C16 fatty acids as substrates to produce C18 fatty acids.

It is expected that the *M. alpina* ELO3 will be suitable to increase carbon flux into the ω-3/ω-6 fatty acid biosynthetic pathway and thereby increase longer-chain fatty acid oil content in engineered *Yarrowia* strains. Thus, one embodiment of the invention is a method of altering fatty acid profiles in an oleaginous yeast, whereby the *M. alpina* ELO3 is expressed alone or in combination with other PUFA biosynthetic pathway genes (e.g., Δ9 desaturase, Δ12 desaturase, Δ6 desaturase, $C_{18/20}$ fatty acid elongase, Δ5 desaturase, Δ17 desaturase, $C_{20/22}$ fatty acid elongase, Δ4 desaturase, Δ15 desaturase, Δ9 fatty acid elongase and/or Δ8 desaturase) to enable increased production of long-chain PUFAs (e.g., LA, ALA, EDA, GLA, STA, ETrA, DGLA, ETA, ARA, EPA, DPA and/or DHA).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, *Experiments with Gene Fusions*; Cold Spring Harbor Laboratory: Cold Spring Harbor, N.Y. (1984); and 3.) Ausubel, F. M. et al., *Current Protocols in Molecular Biology*, published by Greene Publishing Assoc. and Wiley-Interscience (1987).

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, $2^{nd}$ ed., Sinauer Associates: Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.), unless otherwise specified.

*E. coli* TOP10 cells and *E. coli* Electromax DH10B cells were obtained from Invitrogen (Carlsbad, Calif.). Max Efficiency competent cells of *E. coli* DH5α were obtained from GIBCO/BRL (Gaithersburg, Md.). *E. coli* (XL1-Blue) competent cells were purchased from the Stratagene Company (San Diego, Calif.). All *E. coli* strains were typically grown at 37° C. on Luria Bertani (LB) plates.

General molecular cloning was performed according to standard methods (Sambrook et al., supra). Oligonucleotides were synthesized by Sigma-Genosys (Spring, Tex.). PCR products were cloned into Promega's pGEM-T-easy vector (Madison, Wis.).

DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Cultivation of *Yarrowia lipolytica*

*Yarrowia lipolytica* strains ATCC #76982 and ATCC #90812 were purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Yarrowia lipolytica* was performed according to the method of Chen, D. C. et al. (*Appl. Microbiol Biotechnol.* 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. Then, approximately 500 ng of linearized plasmid DNA was incubated in 100 μl of resuspended cells, and maintained at 39° C.

for 1 hr with vortex mixing at 15 min intervals. The cells were plated onto selection media plates and maintained at 30° C. for 2 to 3 days.

For selection of transformants, minimal medium ("MM") was generally used, wherein the composition of MM is as follows: 0.17% yeast nitrogen base (DIFCO Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoro-orotic acid ("FOA"; also 5-fluorouracil-6-carboxylic acid monohydrate) selection media, comprising: 0.17% yeast nitrogen base (DIFCO Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Finally, High Glucose Media ("HGM") was prepared as follows: 14 g/L $KH_2PO_4$, 4 g/L $K_2HPO_4$, 2 g/L $MgSO_4.7H_2O$, 80 g/L glucose (pH 6.5). This media was designed to promote conditions of oleaginy, Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G., and Nishida I. *Arch Biochem Biophys*. 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

Construction of a *Mortierella alpina* cDNA Library

The present Example describes the construction of a cDNA library of *Mortierella alpina* using the BD-Clontech Creator Smart® cDNA library kit (Mississauga, ON, Canada), according to the manufacturer's protocol.

Specifically, *M. alpina* strain ATCC #16266 was grown in 60 mL YPD medium (2% Bacto-yeast extract, 3% Bactor-peptone, 2% glucose) for 3 days at 23° C. Cells were pelleted by centrifugation at 3750 rpm in a Beckman GH3.8 rotor for 10 min and resuspended in 6×0.6 mL Trizole reagent (Invitrogen). Resuspended cells were transferred to six 2 mL screw cap tubes each containing 0.6 mL of 0.5 mm glass beads. The cells were homogenized at the HOMOGENIZE setting on a Biospec (Bartlesville, Okla.) mini bead beater for 2 min. The tubes were briefly spun to settle the beads. Liquid was transferred to 4 fresh 1.5 mL microfuge tubes and 0.2 mL chloroform/isoamyl alcohol (24:1) was added to each tube. The tubes were shaken by hand for 1 min and let stand for 3 min. The tubes were then spun at 14,000 rpm for 10 min at 4° C. The upper layer was transferred to 4 new tubes. Isopropyl alcohol (0.5 mL) was added to each tube. Tubes were incubated at room temperature for 15 min, followed by centrifugation at 14,000 rpm and 4° C. for 10 min. The pellets were washed with 1 mL each of 75% ethanol (made with RNase-free water) and air-dried. The total RNA sample was then redissolved in 500 µl of water, and the amount of RNA was measured by A260 nm using 1:50 diluted RNA sample. A total of 3.14 mg RNA was obtained.

This total RNA sample was further purified with the Qiagen RNeasy total RNA Midi kit following the manufacturer's protocol. Thus, the total RNA sample was diluted to 2 mL and mixed with 8 mL of buffer RLT with 80 µl of β-mercaptoethanol and 5.6 mL 100% ethanol. The sample was divided into 4 portions and loaded onto 4 RNeasy midid columns. The columns were then centrifuged for 5 min at 4500×g. To wash the columns, 2 mL of buffer RPE was loaded and the columns centrifuged for 2 min at 4500×g. The washing step was repeated once, except that the centrifugation time was extended to 5 min. Total RNA was eluted by applying 250 µl of RNase-free water to each column, waiting for 1 min and centrifuging at 4500×g for 3 min.

PolyA(+)RNA was then isolated from the above total RNA sample, following the protocol of Amersham Biosciences' mRNA Purification Kit. Briefly, 2 oligo-dT-cellulose columns were used. The columns were washed twice with 1 mL each of high salt buffer. The total RNA sample from the previous step was diluted to 2 mL total volume and adjusted to 10 mM Tris/HCl, pH 8.0, 1 mM EDTA. The sample was heated at 65° C. for 5 min, then placed on ice. Sample buffer (0.4 mL) was added and the sample was then loaded onto the two oligo-dT-cellulose columns under gravity feed. The columns were centrifuged at 350×g for 2 min, washed 2× with 0.25 mL each of high salt buffer, each time followed by centrifugation at 350×g for 2 min. The columns were further washed 3 times with low salt buffer, following the same centrifugation routine. Poly(A)+RNA was eluted by washing the column 4 times with 0.25 mL each of elution buffer preheated to 65° C., followed by the same centrifugation procedure. The entire purification process was repeated once. Purified poly(A)+RNA was obtained with a concentration of 30.4 ng/µl.

cDNA was generated, using the LD-PCR method specified by BD-Clontech and 0.1 µg of polyA(+) RNA sample. Specifically, for $1^{st}$ strand cDNA synthesis, 3 µl f the poly(A)+ RNA sample was mixed with 1 µl of SMART IV oligo nucleotide (SEQ ID NO:3) and 1 µl of CDSIII/3' PCR primer (SEQ ID NO:4). The mixture was heated at 72° C. for 2 min and cooled on ice for 2 min. To the tube was added the following: 2 µl first strand buffer, 1 µl 20 mM DTT, 1 µl 10 mM dNTP mix and 1 µl Powerscript reverse transcriptase. The mixture was incubated at 42° C. for 1 hr and cooled on ice.

The $1^{st}$ strand cDNA synthesis mixture was used as template for the PCR reaction. Specifically, the reaction mixture contained the following: 2 µl of the $1^{st}$ strand cDNA mixture, 2 µl 5'-PCR primer (SEQ ID NO:5), 2 µl CDSIII/3'-PCR primer (SEQ ID NO:4), 80 µl water, 10 µl 10× Advantage 2 PCR buffer, 2 µl 50× dNTP mix and 2 µl 50× Advantage 2 polymerase mix. The thermocycler conditions were set for 95° C. for 20 sec, followed by 14 cycles of 95° C. for 5 sec and 68° C. for 6 min on a GenAmp 9600 instrument. PCR product was quantitated by agarose gel electrophoresis and ethidium bromide staining.

Seventy-five µl of the above PCR products (cDNA) were mixed with 3 µl of 20 µg/µl proteinase K supplied with the kit. The mixture was incubated at 45° C. for 20 min, then 75 µl of water was added and the mixture was extracted with 150 µl phenol:chloroform:isoamyl alcohol mixture (25:24:1). The aqueous phase was further extracted with 150 µl chloroform:

isoamyl alcohol (25:1). The aqueous phase was then mixed with 15 µl of 3 M sodium acetate, 2 µl of 20 µl/µl glycogen and 400 µl of 100% ethanol. The mixture was immediately centrifuged at room temperature for 20-min at 14000 rpm in a microfuge. The pellet was washed once with 150 µl of 80% ethanol, air dried and dissolved in 79 µl of water.

Dissolved cDNA was subsequently digested with SfiI (79 µl of the cDNA was mixed with 10 µl of 10× SfiI buffer, 10 µl of SfiI enzyme and 1 µl of 100× BSA and the mixture was incubated at 50° C. for 2 hrs). Xylene cyanol dye (2 µl of 1%) was added. The mixture was then fractionated on the Chroma Spin-400 column provided with the kit, following the manufacturer's procedure exactly. Fractions collected from the column were analyzed by agarose gel electrophoresis. The first three fractions containing cDNA were pooled and cDNA precipitated with ethanol. The precipitated cDNA was redissolved in 7 µl of water, and ligated into kit-supplied pDNR-LIB.

Library Sequencing

The ligation products were used to transform E. coli XL-1 Blue electroporation competent cells (Stratagene). An estimated total of $2 \times 10^6$ colonies was obtained. Sequencing of the cDNA library was carried out by Agencourt Bioscience Corporation (Beverly, Mass.), using an M13 forward primer (SEQ ID NO:6).

Example 2

Identification of a Partial Fatty Acid Elongase Sequence From *Mortierella alpina*

The present Example describes the identification of a cDNA fragment (SEQ ID NO:7) encoding a portion of a *M. alpina* fatty acid elongase, from among 9,984 cDNA sequences.

Identity of the sequence was determined by conducting BLAST (Basic Local Alignment Search Tool; Altschul, S. F., et al., *J. Mol. Biol.* 215:403-410 (1993)) searches of *M. alpina* cDNA sequences for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). cDNA sequences were translated in all reading frames and compared for similarity to all publicly available protein sequences contained in the "nr" database, using the BLASTX algorithm (Gish, W. and States, D. J. *Nature Genetics* 3:266-272 (1993)) provided by the NCBI. One cDNA fragment (SEQ ID NO:7) bore significant homology to a number of fatty acid elongases and thus was tentatively identified as an elongase.

The results of the BLAST comparison summarizing the sequence to which SEQ ID NO:7 had the most similarity are reported according to the % identity, % similarity, and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance. Thus, the translated amino acid sequence of SEQ ID NO:7 had 32% identity and 46% similarity with the protein sequence of a potential fatty acid elongase from *Candida albicans* SC5314 (GenBank Accession No. EAL04510.1, annotated therein as one of three potential fatty acid elongase genes similar to *S. cerevisiae* EUR4, FEN1 and ELO1), with an expectation value of 4e-13. Additionally, SEQ ID NO:7 had 35% identity and 53% similarity with ELO1 from *Saccharomyces cerevisiae* (GenBank Accession No. NC_001142, bases 67849-68781 of chromosome X). The *S. cerevisiae* ELO1 is described as a medium-chain acyl elongase, that catalyzes carboxy-terminal elongation of unsaturated C12-C16 fatty acyl-CoAs to C16-C18 fatty acids.

On the basis of the homologies reported above, the *Yarrowia lipolytica* gene product of SEQ ID NO:7 was designated herein as "elongase 3" or "ELO3".

Example 3

Sequencing of the Complete *M. alpina* ELO3

Analysis of the partial fatty acid elongase cDNA sequence (SEQ ID NO:7) indicated that the 5' and 3'-ends were both incomplete. To obtain the missing regions, genome-walking techniques were utilized.

Genome Walking to Isolate the 3'-End Region of *M. alpina* ELO3

A Clontech Universal GenomeWalker™ kit was used to obtain a piece of genomic DNA corresponding to the 3'-end region of the *M. alpina* ELO3. Briefly, 2.5 µg each of *M. alpina* genomic DNA was digested with DraI, EcoRV, PvuII or StuI individually, the digested DNA samples were purified using Qiagen Qiaquick PCR purification kits and eluted with 30 µl each of kit buffer EB, and the purified samples were then ligated with Genome Walker adaptor (SEQ ID NOs:8 [top strand] and 9 [bottom strand]), as shown below:

```
5'-GTAATACGACTCACTATAGGGCACGCGTGGTCGACGGCCCGGGCTGG
T-3'

3'-H2N-CCCGACCA-5'
```

Each ligation reaction mixture contained 1.9 µl of 25 µM Genome Walker adaptor, 1.6 µl 10× ligation buffer, 0.5 µl T4 DNA ligase and 4 µl of one of the purified digested genomic DNA samples. The reaction mixtures were incubated at 16° C. overnight. The reaction was terminated by incubation at 70° C. for 5 min. Then, 72 µl of 10 mM TrisHCl, 1 mM EDTA, pH 7.4 buffer was added to each ligation reaction mix.

Four separate PCR reactions were performed, each using one of the four ligation mixtures as template. The PCR reaction mixtures contained 1 µl of ligation mixture, 0.5 µl of 20 µM primer MA Elong 3'1 (SEQ ID NO:10), 1 µl of 10 µM kit primer AP1 (SEQ ID NO:11), 22.5 µl water, and 25 µl ExTaq premix Taq 2× PCR solution (TaKaRa Bio Inc., Otsu, Shiga, 520-2193, Japan). The PCR reactions were carried out for 32 cycles using the following conditions: denaturation at 94° C. for 30 sec, annealing at 55° C. for 30 sec, and elongation at 72° C. for 3 min. A final elongation cycle at 72° C. for 7 min was carried out, followed by reaction termination at 4° C.

The products of each PCR reaction were diluted 1:50 individually and used as templates for a second round of PCR. Each reaction mixture contained 1 µl of one of the diluted PCR products as template, 0.5 µl of 20 µM primer MA elong 3'2 (SEQ ID NO:12), 1 µl of 10 µM kit primer AP2 (SEQ ID NO:13), 22.5 µl water and 25 µl of ExTaq premix Taq 2× PCR solution (TaKaRa). PCR reactions were carried out for 32 cycles using the same thermocycler conditions described above.

A 1041 bp DNA fragment was obtained from the second round of PCR (SEQ ID NO:14). This fragment was purified and cloned into pCR2.1-TOPO and sequenced. Sequence analysis showed that the fragment contained the 3'-end of ELO3, including ~640 bp downstream of the 'TAA' stop codon of the gene.

Genome Walking to Isolate the 5'-End Region of *M. alpina* ELO3

The same set of four ligation mixtures used in the Clontech 3'-end RACE (supra) were also used to obtain the 5'-end region of the *M. alpina* ELO3. Specifically, a first round of PCR using the same components and conditions as described above was conducted, with the exception that MA Elong 5'1 (SEQ ID NO:15, nested at the 5' end) and AP1 were used as primers (i.e., instead of primers MA Elong 3'1 and AP1). The second round of PCR used MA Elong 5'2 (SEQ ID NO:16, nested at the 5' end) and AP2 as primers. A 2223 bp DNA fragment (SEQ ID NO:17) was obtained. It was purified and cloned into pCR2.1-TOPO and sequenced. Analysis of the sequence showed that it contained the 5'-region of the ELO3 gene.

Thus, the entire cDNA sequence of the *M. alpina* ELO3 (SEQ ID NO:1) was obtained by combining the original partial cDNA sequence (SEQ ID NO:7) with the overlapping 5' and 3' sequences obtained by genome walking (SEQ ID NOs:14 and 17, respectively; graphically illustrated in FIG. 1). This yielded a sequence of 3557 bp, identified herein as SEQ ID NO:18, comprising: 2091 bp upstream of the putative 'ATG' translation initiation codon of ELO3; the 828 bp ELO3 ORF (i.e., SEQ ID NO:1, corresponding to bases 2092-2919 of SEQ ID NO:18); and, 638 bp downstream of the ELO3 stop codon (corresponding to bases 2920-3557 of SEQ ID NO:18).

The corresponding genomic sequence of the *M. alpina* ELO3 is longer than the cDNA fragment provided as SEQ ID NO:18. Specifically, a 542 bp intron (SEQ ID NO:19) was found in the genomic DNA containing the ELO3 gene at 318 bp of the ORF; thus, the genomic DNA fragment, provided herein as SEQ ID NO:29, is 4,099 bp (FIG. 1).

The translated ELO3 protein sequence (SEQ ID NO:2) had the following homology to known fatty acid elongase, based on BLAST program analysis (supra, Example 2): 37% identity and 51% similarity to the potential fatty acid elongase from *Candida albicans* SC5314 (GenBank Accession No. EAL04510.1), with an expectation value of 4e-43. Additionally, the translated ELO3 shared 33% identity and 44% similarity with the protein sequence of XP_331368 (annotated therein as a "hypothetical protein") from Neurospora crassa, with an expectation value of 3e-44.

Example 4

Generation of *Yarrowia lipolytica* ATCC #20362 Strain Y2031

The present Example describes the construction of strain Y2031, derived from *Yarrowia lipolytica* ATCC #20362. Y2031 strain was generated by integration of a TEF::Y.Δ12::Pex20 chimeric gene from plasmid pKUNT2 into the Ura3 gene locus of ATCC #20362, thereby resulting in a Ura- genotype. Plasmid pKUNT2 contained the following components:

TABLE 3

Description of Plasmid PKUNT2 (SEQ ID NO: 20)

| RE Sites And Nucleotides Within SEQ ID NO: 20 | Description Of Fragment And Chimeric Gene Components |
|---|---|
| AscI/BsiWI (3225-3015) | 784 bp 5' part of *Yarrowia* Ura3 gene (GenBank Accession No. AJ306421) |
| SphI/PacI (5933-13) | 516 bp 3' part of *Yarrowia* Ura3 gene (GenBank Accession No. AJ306421) |
| EcoRI/BsiWI (6380-8629) | TEF::Y.Δ12::Pex20, comprising: TEF: TEF promoter (GenBank Accession No. AF054508) Y.Δ12: *Yarrowia* Δ12 desaturase gene (SEQ ID NO: 21) Pex20: Pex20 terminator sequence from *Yarrowia* Pex20 gene (GenBank Accession No. AF054613) |

The pKUNT2 plasmid was digested with AscI/SphI, and then used for transformation of wild type *Y. lipolytica* ATCC #20362 according to the General Methods. The transformant cells were plated onto FOA selection media plates and maintained at 30° C. for 2 to 3 days. The FOA resistant colonies were picked and streaked onto MM and MMU selection plates. The colonies that could grow on MMU plates but not on MM plates were selected as Ura-strains. Single colonies (5) of Ura-strains were then inoculated into liquid MMU at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 45% LA in two Ura—strains (strains #2 and #3), compared to about 20% LA in the wild type ATCC #20362. Transformant strain #2 was designated as strain "Y2031".

Example 5

Heterologous Expression of the *Mortierella alpina* Fatty Acid ELO3 in *Yarrowia lipolytica* Strain Y2031

The present Example describes the over-expression of the *M. alpina* ELO3 ORF in a chimeric gene under the control of a *Y. lipolytica* promoter in *Y. lipolytica* strain Y2031, and the effect of the over-expression as determined by an analysis of TAG content.

Construction of Plasmid pZUF6S-E3WT. Comprising A FBAIN::ELO3::PEX16-3' Chimeric Gene The *M. alpina* fatty acid ELO3 ORF was cloned as follows. Primers MA Elong 5' NcoI 3 and MA Elong 3" NotI (SEQ ID NOs:23 and 24) were used to amplify the ELO3 ORF from the cDNA of *M. alpina* (Example 1) by PCR. The reaction mixture contained 1 μl of the cDNA, 1 μl each of the primers, 22 μl water and 25 μl ExTaq premix 2× Taq PCR solution (TaKaRa). Amplification was carried out as follows: initial denaturation at 94° C. for 30 sec, followed by 32 cycles of denaturation at 94° C. for 30 sec, annealing at 55° C. for 30 sec and elongation at 72° C. for 120 sec. A final elongation cycle at 72° C. for 7 min was carried out, followed by reaction termination at 4° C. An ~830 bp DNA fragment was obtained from the PCR reaction. It was purified using a Qiagen (Valencia, Calif.) PCR purification kit according to the manufacturer's protocol. The purified PCR product was divided into two aliquots, wherein one was digested with NcoI and NspI, while the other with NspI and NotI. The ~270 bp NcoI-NspI and ~560 bp NspI-NotI fragments were cloned into NcoI-NotI cut pZF5T-PPC vector (FIG. 2A; SEQ ID NO:25) by three-piece ligation, such that the gene was under the control of the *Y. lipolytica* FBAIN promoter and the PEX16-3' terminator region (GenBank Accession No. U75433) in the auto-replicating vector for expression in *Y. lipolytica*. The "FBAIN promoter" refers to the 5' upstream untranslated region in front of the 'ATG' translation initiation codon of a fructose-bisphosphate aldolase enzyme (E.C. 4.1.2.13) encoded by the fba1 gene gene and that is necessary for expression, plus a portion of 5' coding region that has an intron of the fba1 gene (see WO 2005/049805 for further details). Correct transformants were confirmed by miniprep analysis and the resultant plasmid was designated as "pZF5T-PPC-E3" (SEQ ID NO:26).

Plasmid pZF5T-PPC-E3 was digested with ClaI and PacI and the ~2.2 kB band (i.e., the FBAIN::ELO 3::PEX16-3' fragment) was purified from an agarose gel using a Qiagen gel extraction kit. The fragment was cloned into ClaI-PacI cut pZUF6S (FIG. 2B; SEQ ID NO:27), an auto-replication plasmid containing the *Mortierella alpina* Δ6 desaturase ORF ("D6S"; GenBank Accession No. AF465281) under the control of the FBAIN promoter with a Pex20-3' terminator (i.e., a FBAIN::D6S::Pex20 chimeric gene) and a Ura3 gene. Correct transformants were confirmed by miniprep analysis and the resultant plasmid was designated as "pZUF6S-E3WT" (SEQ ID NO:28; FIG. 2C).

Analysis of Lipid Content in Transformant *Y. lipolytica* Over-Expressing the *M. alpina* ELO3

*Y. lipolytica* strain Y2031 was transformed with plasmid pZUF6S (control, comprising a FBAIN::D6S::Pex20 chimeric gene) and plasmid pZUF6S-E3WT (comprising a FBAIN::D6S::Pex20 chimeric gene and the FBAIN::ELO 3::PEX16 chimeric gene) according to the General Methods. Transformants were grown for 2 days in synthetic MM supplemented with amino acids, followed by 4 days in HGM. The fatty acid profile of six clones containing pZUF6S (clones #1-6, from a single transformation) and 22 clones (from four different transformations [i.e., #3, 5, 6, and 7]) containing pZUF6S-E3WT are shown below in Table 4, based on GC analysis (as described in the General Methods). Fatty acids are identified as 16:0 (palmitate), 16:1 (palmitoleic acid), 18:0, 18:1 (oleic acid), 18:2 (LA) and GLA; and the composition of each is presented as a % of the total fatty acids.

TABLE 4

Lipid Content In *Yarrowia* Strain Y2031 Engineered To Over-Express *M. alpina* Fatty Acid ELO3

| *Y. lipolytica* Strain Y2031 Transformant And/Or Clone No. | Fatty Acid Composition (% Of Total Fatty Acids) | | | | | |
|---|---|---|---|---|---|---|
| | 16:0 | 16:1 | 18:0 | 18:1 | 18:2 | GLA |
| pZUF6S #1 (control) | 9.0 | 23.2 | 1.2 | 38.2 | 19.8 | 6.9 |
| PZUF6S #2 (control) | 10.1 | 23.4 | 1.4 | 39.0 | 17.5 | 7.1 |
| pZUF6S #3 (control) | 9.7 | 22.7 | 1.4 | 39.0 | 20.2 | 7.0 |
| pZUF6S #4 (control) | 8.5 | 24.1 | 0.0 | 40.8 | 19.8 | 6.9 |
| pZUF6S #5 (control) | 9.8 | 22.4 | 1.7 | 39.1 | 20.2 | 6.8 |
| pZUF6S #6 (control) | 9.1 | 22.7 | 1.9 | 39.9 | 19.7 | 6.6 |
| PZUF6S-E3WT #3-1 | 8.9 | 17.3 | 4.1 | 36.5 | 21.6 | 11.6 |
| PZUF6S-E3WT #3-2 | 8.8 | 17.8 | 3.7 | 36.9 | 21.3 | 11.5 |
| *pZUF6S-E3WT #3-3* | *8.9* | *18.3* | *3.5* | *33.8* | *35.4* | *0.0* |
| PZUF6S-E3WT #3-6 | 8.5 | 19.9 | 4.4 | 37.8 | 17.1 | 12.3 |
| PZUF6S-E3WT #5-1 | 8.6 | 17.6 | 4.0 | 37.6 | 21.1 | 11.1 |
| PZUF6S-E3WT #5-2 | 8.8 | 17.1 | 3.9 | 37.6 | 21.3 | 11.2 |
| PZUF6S-E3WT #5-3 | 9.1 | 17.1 | 3.5 | 37.6 | 21.5 | 11.1 |
| PZUF6S-E3WT #5-4 | 8.8 | 17.9 | 4.3 | 38.0 | 19.3 | 11.7 |
| PZUF6S-E3WT #5-5 | 9.2 | 16.1 | 4.4 | 37.0 | 21.6 | 11.7 |
| *pZUF6S-E3WT #5-6* | *8.7* | *21.5* | *4.2* | *30.3* | *35.3* | *0.0* |
| PZUF6S-E3WT #6-1 | 9.4 | 16.9 | 4.6 | 36.6 | 21.5 | 11.0 |
| PZUF6S-E3WT #6-2 | 9.8 | 16.2 | 4.1 | 36.5 | 21.9 | 11.6 |
| PZUF6S-E3WT #6-3 | 9.4 | 17.0 | 4.4 | 36.2 | 21.8 | 11.3 |
| PZUF6S-E3WT #6-4 | 8.3 | 16.6 | 4.2 | 36.9 | 21.9 | 12.2 |
| PZUF6S-E3WT #6-5 | 8.8 | 18.5 | 5.5 | 36.0 | 17.8 | 13.4 |
| PZUF6S-E3WT #6-6 | 8.7 | 19.5 | 5.2 | 35.4 | 18.1 | 13.2 |
| *pZUF6S-E3WT #7-1* | *0.0* | *30.6* | *0.0* | *35.5* | *18.2* | *15.8* |
| PZUF6S-E3WT #7-2 | 8.0 | 17.7 | 4.0 | 37.7 | 20.9 | 11.7 |
| *pZUF6S-E3WT #7-3* | *0.0* | *26.7* | *4.2* | *36.0* | *21.4* | *11.7* |
| *pZUF6S-E3WT #7-4* | *0.0* | *28.1* | *4.3* | *37.0* | *16.9* | *13.6* |
| PZUF6S-E3WT #7-5 | 8.3 | 17.0 | 4.7 | 36.7 | 21.2 | 12.1 |
| PZUF6S-E3WT #7-6 | 8.0 | 18.0 | 4.8 | 36.3 | 20.8 | 12.1 |

Some of the samples (labeled in bold and italics) deviated from expected readings. Specifically, neither Y2031+pZUF6S-E3WT #3-3 nor Y2031+pZUF6S-E3WT #5-6 produced GLA. Similarly, Y2031+pZUF6S-E3WT #7-1, #7-3 and #7-4 had GC errors, wherein the 16:0 and 16:1 peaks were read by the GC as a single peak. As a result of these variant results, Table 5 reports the average lipid in the control and transformant strains expressing ELO3. Specifically, Table 5 shows the averages from the fatty acid profiles in Table 4, although the lines indicated by bold and italics as being incorrect in Table 4 were not included when calculating these averages. "Total C16" represents the sum of the average areas of 16:0 and 16:1, while "Total C18" reflects the sum of the average areas of 18:0, 18:1, 18:2 and GLA.

TABLE 5

Average Lipid Content In *Yarrowia* Strain Y2031 Engineered To Over-Express *M. alpina* Fatty Acid ELO3

| *Y. lipolytica* Strain Y2031 Transformant | Average Fatty Acid Composition (% Of Total Fatty Acids) | | | | | | Total C16 | Total C18 |
|---|---|---|---|---|---|---|---|---|
| | 16:0 | 16:1 | 18:0 | 18:1 | 18:2 | GLA | | |
| pZUF6S (control) | 9.4 | 23.1 | 1.3 | 39.3 | 19.5 | 6.9 | 32.4 | 67.1 |
| PZUF6S-E3WT #3 | 8.7 | 18.3 | 4.1 | 37.1 | 20.0 | 11.8 | 27.0 | 73.0 |
| PZUF6S-E3WT #5 | 8.9 | 17.2 | 4.0 | 37.6 | 21.0 | 11.4 | 26.1 | 73.9 |
| pZUF6S-E3WT #6 | 9.1 | 17.5 | 4.6 | 36.3 | 20.5 | 12.1 | 26.5 | 73.5 |
| PZUF6S-E3WT #7 | 8.1 | 17.6 | 4.5 | 36.9 | 21.0 | 12.0 | 25.6 | 74.4 |

Based on the data reported above, overexpression of the *M. alpina* ELO3 resulted in an increased percentage of C18 and a reduced percentage of C16 when co-expressed with a *M. alpina* Δ6 desaturase in *Yarrowia lipolytica* strain Y2031, relative to a control strain of Y2031 overexpressing the *M. alpina* Δ6 desaturase only. This indicated that the *M. alpina* ELO3 was indeed a $C_{16/18}$ fatty acid elongase.

It will be obvious to one of skill in the art that other chimeric genes could be co-expressed with the *M. alpina* ELO3 gene in engineered *Yarrowia* to increase production of various other fatty acids. For example, in addition to the *M. alpina* ELO3 (which could optionally be codon-optimized for increased expression), one could readily express a $C_{14/16}$ fatty acid elongase and/or a Δ9 desaturase as a means to permit the up-regulation of carbon flow into lipid metabolism. In alternate embodiments, the *M. alpina* ELO3 could readily be co-expressed with any of the following PUFA biosynthetic pathway genes, including e.g., a Δ12 desaturase, a Δ15 desaturase, a Δ6 desaturase, a Δ5 desaturase, a Δ17 desaturase, a Δ9 fatty acid elongase, a Δ8 desaturase, a $C_{18/20}$ fatty acid elongase, a $C_{20/22}$ fatty acid elongase and/or a Δ4 desaturase, to enable increased production of various PUFAs (FIG. 3).

What is claimed is:

1. An isolated nucleic acid molecule encoding a $C_{16/18}$ fatty acid elongase enzyme, selected from the group consisting of:
   (a) an isolated nucleic acid molecule encoding the amino acid sequence as set forth in SEQ ID NO:2 and
   (b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or,
   an isolated nucleic acid molecule that is completely complementary to (a) or (b).

2. The isolated nucleic acid molecule of claim 1 as set forth in SEQ ID NO: 1.

3. An isolated nucleic acid molecule comprising a first nucleotide sequence encoding a $C_{16/18}$ fatty acid elongase enzyme of at least 275 amino acids that has at least 95% identity based on the BLAST method of alignment when compared to a polypeptide having the sequence as set forth in SEQ ID NO:2; or a second nucleotide sequence comprising the complement of the first nucleotide sequence.

4. A chimeric gene comprising the isolated nucleic acid molecule of claim 1 operably linked to suitable regulatory sequences.

5. An isolated host cell comprising the isolated nucleic acid molecule of claim 1.

6. The isolated host cell of claim 5 selected from the group consisting of algae, bacteria, fungi and yeast.

7. The transformed host cell of claim 6 wherein the yeast is an oleaginous yeast.

8. The transformed host cell of claim 7 wherein the oleaginous yeast cell is selected from the group consisting of: *Yarrowia, Candida, Rhodotorula, Rhodosporidium, Cryptococcus, Trichosporon* and *Lipomyces*.

9. The transformed host cell of claim 8 wherein the host cell is *Yarrowia lipolytica*.

\* \* \* \* \*

SEQUENCE LISTING

<160> NUMBER OF SEQ ID NOS: 29

<210> SEQ ID NO 1
<211> LENGTH: 828
<212> TYPE: DNA
<213> ORGANISM: Mortierella alpina

<400> SEQUENCE: 1

```
atggagtctg acctatgcc tgccgggatc ccctcccctg aatactatga ctttttcatg      60
gactggaaga caccccctggc aattgctgcc acctacaccg ccgctgttgg gctcttcaac     120
cccaaggttg gcaaagtctc gcgcgtggta gccaagtcgg ctaacgccaa gccggcagag     180
cgcacgcagt ccggcgccgc catgaccgcc tttgtctttg tccacaacct tatcctctgc     240
gtgtactctg gaatcacctt ctactacatg ttcccagcca tggtcaagaa ctttagaaca     300
cataccctcc atgaggccta ctgcgatacg gatcagagcc tgtggaacaa cgcccttggc     360
tactggggct acctcttcta cctttcaaag ttttacgagg tcattgacac catcatcatc     420
atcttgaagg ggcgccgctc gtccctgctc cagacctacc accacgccgg cgctatgatc     480
accatgtggt ccggcatcaa ctaccaggca acgcccattt ggattttgt cgtcttcaac     540 tcgttcatcc acaccatcat gtactgttac tatgccttca cctcaatcgg cttccacccc     600
ccaggcaaga agtacctcac ctccatgcag atcacccagt ttttggtcgg catcactatc     660
gccgtctctt atctcttcgt ccctggatgt atccgcacac ccggtgctca gatggctgtc     720
tggatcaacg tcggatacct ctttcccctc acttatctct tgtggattt tgccaagcgt     780 acttactcca agcgtagtgc catcgccgct cagaagaagg cccagtaa                828
```

<210> SEQ ID NO 2
<211> LENGTH: 275
<212> TYPE: PRT
<213> ORGANISM: Mortierella alpina

<400> SEQUENCE: 2

```
Met Glu Ser Gly Pro Met Pro Ala Gly Ile Pro Phe Pro Glu Tyr Tyr
1               5                   10                  15

Asp Phe Phe Met Asp Trp Lys Thr Pro Leu Ala Ile Ala Ala Thr Tyr
            20                  25                  30

Thr Ala Ala Val Gly Leu Phe Asn Pro Lys Val Gly Lys Val Ser Arg
        35                  40                  45

Val Val Ala Lys Ser Ala Asn Ala Lys Pro Ala Glu Arg Thr Gln Ser
    50                  55                  60

Gly Ala Ala Met Thr Ala Phe Val Phe Val His Asn Leu Ile Leu Cys
65                  70                  75                  80
```

```
Val Tyr Ser Gly Ile Thr Phe Tyr Tyr Met Phe Pro Ala Met Val Lys
                85                  90                  95

Asn Phe Arg Thr His Thr Leu His Glu Ala Tyr Cys Asp Thr Asp Gln
            100                 105                 110

Ser Leu Trp Asn Asn Ala Leu Gly Tyr Trp Gly Tyr Leu Phe Tyr Leu
        115                 120                 125

Ser Lys Phe Tyr Glu Val Ile Asp Thr Ile Ile Ile Leu Lys Gly
    130                 135                 140

Arg Arg Ser Ser Leu Leu Gln Thr Tyr His His Ala Gly Ala Met Ile
145                 150                 155                 160

Thr Met Trp Ser Gly Ile Asn Tyr Gln Ala Thr Pro Ile Trp Ile Phe
                165                 170                 175

Val Val Phe Asn Ser Phe Ile His Thr Ile Met Tyr Cys Tyr Tyr Ala
                180                 185                 190

Phe Thr Ser Ile Gly Phe His Pro Pro Gly Lys Lys Tyr Leu Thr Ser
            195                 200                 205

Met Gln Ile Thr Gln Phe Leu Val Gly Ile Thr Ile Ala Val Ser Tyr
        210                 215                 220

Leu Phe Val Pro Gly Cys Ile Arg Thr Pro Gly Ala Gln Met Ala Val
225                 230                 235                 240

Trp Ile Asn Val Gly Tyr Leu Phe Pro Leu Thr Tyr Leu Phe Val Asp
                245                 250                 255

Phe Ala Lys Arg Thr Tyr Ser Lys Arg Ser Ala Ile Ala Ala Gln Lys
            260                 265                 270

Lys Ala Gln
        275

<210> SEQ ID NO 3
<211> LENGTH: 39
<212> TYPE: DNA
<213> ORGANISM: Artificial Sequence
<220> FEATURE:
<223> OTHER INFORMATION: SMART IV oligonucleotide

<400> SEQUENCE: 3
aagcagtggt atcaacgcag agtggccatt acggccggg                     39

<210> SEQ ID NO 4
<211> LENGTH: 59
<212> TYPE: DNA
<213> ORGANISM: Artificial Sequence
<220> FEATURE:
<223> OTHER INFORMATION: CDSIII/3'PCR primer
<220> FEATURE:
<221> NAME/KEY: misc_feature
<222> LOCATION: (28)..(57)
<223> OTHER INFORMATION: thymidine (dT); see BD Biosciences Clontech's
      SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 4
attctagagg ccgaggcggc cgacatgttt tttttttttt tttttttttt tttttttvn    59

<210> SEQ ID NO 5
<211> LENGTH: 23
<212> TYPE: DNA
<213> ORGANISM: Artificial Sequence
<220> FEATURE:
<223> OTHER INFORMATION: 5'-PCR primer
```

<400> SEQUENCE: 5
aagcagtggt atcaacgcag agt                                                23

<210> SEQ ID NO 6
<211> LENGTH: 18
<212> TYPE: DNA
<213> ORGANISM: Artificial Sequence
<220> FEATURE:
<223> OTHER INFORMATION: Primer M13

<400> SEQUENCE: 6
tgtaaaacga cggccagt                                                      18

<210> SEQ ID NO 7
<211> LENGTH: 607
<212> TYPE: DNA
<213> ORGANISM: Mortierella alpina
<220> FEATURE:
<221> NAME/KEY: misc_feature
<222> LOCATION: (133)..(135)
<223> OTHER INFORMATION: ATG translation initiation codon

<400> SEQUENCE: 7
cccgtcttca ccctccctct tcccccccgtt cctacgtcta cagccgttgg ctcatcttgc         60
agttgcttgt ctactatttg gtgccgacct atattcctct gtcacccaac ctaccgcact        120
cacactcgca taatggagtc tggacctatg cctgccggga tccccttccc tgaatactat        180 gacttttca tggactggaa gacacccctg gcaattgctg ccacctacac cgccgctgtt        240
gggctcttca cccccaaggt tggcaaagtc tcgcgcgtgg tagccaagtc ggctaacgcc        300
aagccggcag agcgcacgca gtccggcgcc gccatgaccg cctttgtctt tgtccacaac        360
cttatcctct gcgtgtactc tggaatcacc ttctactaca tgttcccagc catggtcaag        420
aactttagaa cacataccct ccatgaggcc tactgcgata cggatcagag cctgtggaac        480
aacgccctcg gctactgggg ctacctcttc tacctttcaa agttttacga ggtcattgac        540
accatcatca tcatcttgaa ggggcgccgc tcgtccctgc tccagaccta ccaccacgcc        600
ggcgcta                                                                 607

<210> SEQ ID NO 8
<211> LENGTH: 44
<212> TYPE: DNA
<213> ORGANISM: Artificial Sequence
<220> FEATURE:
<223> OTHER INFORMATION: Genome Walker adaptor-1

<400> SEQUENCE: 8
gtaatacgac tcactatagg gcac gcgtggtcga cggcccgggc tggt                    44

<210> SEQ ID NO 9
<211> LENGTH: 8
<212> TYPE: DNA
<213> ORGANISM: Artificial Sequence
<220> FEATURE:
<223> OTHER INFORMATION: Genome Walker adaptor-2
<220> FEATURE:
<221> NAME/KEY: misc_feature
<222> LOCATION: (1)..(1)
<223> OTHER INFORMATION: 5' end is associated with a -PO4 group
<220> FEATURE:
<221> NAME/KEY: misc_feature
<222> LOCATION: (8)..(8)
<223> OTHER INFORMATION: 3' end is associated with a -H2N group

```
<400> SEQUENCE: 9 accagccc                                                                8

<210> SEQ ID NO 10
<211> LENGTH: 25
<212> TYPE: DNA
<213> ORGANISM: Artificial Sequence
<220> FEATURE:
<223> OTHER INFORMATION: Primer MA Elong 3'1

<400> SEQUENCE: 10
gatacggatc agagcctgtg gaaca                                            25

<210> SEQ ID NO 11
<211> LENGTH: 22
<212> TYPE: DNA
<213> ORGANISM: Artificial Sequence
<220> FEATURE:
<223> OTHER INFORMATION: Primer AP1

<400> SEQUENCE: 11
gtaatacgac tcactatagg gc                                               22

<210> SEQ ID NO 12
<211> LENGTH: 25
<212> TYPE: DNA
<213> ORGANISM: Artificial Sequence
<220> FEATURE:
<223> OTHER INFORMATION: Primer MA elong 3'2

<400> SEQUENCE: 12
cttctacctt tcaaagtttt acgag                                            25

<210> SEQ ID NO 13
<211> LENGTH: 19
<212> TYPE: DNA
<213> ORGANISM: Artificial Sequence
<220> FEATURE:
<223> OTHER INFORMATION: Primer AP2

<400> SEQUENCE: 13
actatagggc acgcgtggt                                                   19

<210> SEQ ID NO 14
<211> LENGTH: 1042
<212> TYPE: DNA
<213> ORGANISM: Mortierella alpina
<220> FEATURE:
<221> NAME/KEY: misc_feature
<222> LOCATION: (402)..(404)
<223> OTHER INFORMATION: Stop codon

<400> SEQUENCE: 14
tgaaggggcg ccgctcgtcc ctgctccaga cctaccacca cgccggcgct atgatcacca      60
tgtggtccgg catcaactac caggcaacgc ccatttggat ttttgtcgtc ttcaactcgt     120
tcatccacac catcatgtac tgttactatg ccttcacctc aatcggcttc cacccccag      180 gcaagaagta cctcacctcc atgcagatca cccagttttt ggtcggcatc actatcgccg     240
tctcttatct cttcgtccct ggatgtatcc gcacacccgg tgctcagatg gctgtctgga     300
tcaacgtcgg ataccttcttt cccctcactt atctctttgt ggattttgcc aagcgtactt    360
actccaagcg tagtgccatc gccgctcaga agaaggccca gtaaagaggc cacttcttgt     420
cgtttactct actgtttcca acatttacat ctctcaatgg cagcctcctc cctctatcct    480
```

| | |
|---|---|
| tcgcactttc attttagttc cttgtattca taaaargtca aaattcattg taactccaaa | 540 |
| agtgccaatg gctttatcat ggatgagtgc catgtttatg cccattgca tcaatacagg | 600 |
| aagatatgag cggtcagcga tagctattcc tctgagttgt cctggccttg tatgcactct | 660 |
| cgaaggagga aatggatcgg agcatcagca ctatttcagg actaggagag atacatccaa | 720 |
| aattttaaag gcatctctgg tcagtacaag agcgacttgg caacaagtct ttagtcaaac | 780 |
| ttcctcacct ttgaacttcc tcagaggtcg ccgtggcact gtggacggag acccgtgaaa | 840 |
| agaactcatg cagcaggtta agcaaccttg gaaatccatc gatgaatgcc tgatgtaaaa | 900 |
| attgagaagc tgcaagagcc aaaagttcag ttcagcacat ataagagact ttggccaaga | 960 |
| gcgatgaagt cacatgggaa ccacgtaaac aaacctcgtg cggagsacca gcccgggccg | 1020 |
| tcgaccacgc gtgccctata gt | 1042 |

<210> SEQ ID NO 15
<211> LENGTH: 25
<212> TYPE: DNA
<213> ORGANISM: Artificial Sequence
<220> FEATURE:
<223> OTHER INFORMATION: Primer MA Elong 5'1

<400> SEQUENCE: 15

| | |
|---|---|
| gcataggtcc agactccatt atgcg | 25 |

<210> SEQ ID NO 16
<211> LENGTH: 25
<212> TYPE: DNA
<213> ORGANISM: Artificial Sequence
<220> FEATURE:
<223> OTHER INFORMATION: Primer MA Elong 5'2

<400> SEQUENCE: 16

| | |
|---|---|
| cagaggaata taggtcggca ccaaa | 25 |

<210> SEQ ID NO 17
<211> LENGTH: 2223
<212> TYPE: DNA
<213> ORGANISM: Mortierella alpina
<220> FEATURE:
<221> NAME/KEY: misc_feature
<222> LOCATION: (2092)..(2094)
<223> OTHER INFORMATION: ATG translation initiation codon

<400> SEQUENCE: 17

| | |
|---|---|
| actatagggc acgcgtggtc gacggcccgg gctggtccta cctctcaatc ttgttgccct | 60 |
| gtagtcctga aatgagctcg tcatgggtct ctgtcctctc ctcgttatgg tcaaacgcat | 120 |
| tggacccggt tttctttaga ggagcattct tcttgtttaa gccgactcct cttcccgtcc | 180 |
| cgaacgacaa cttgataggt ccaccatttc catttggtgg gtgaagcggg ctgtcctcag | 240 |
| cggacatgac tctgagctag aaggaagggt gtagaggacg aaggagtaag tgctaccgtt | 300 |
| cactggcagg tgaggagcgt cgggtctaag ccacatgcct gccaattgtc ctcgccaagt | 360 |
| gcttggaagg tgtattgatg ctcatgcagc tccactctgg acctggaaac gccaccgcat | 420 |
| cgcattctta atgagctctg ctacaaacga caatctgcga accagtttgc cagggagct | 480 |
| agtcgagtct ggaaagcggg accagtgagt gactcggcgg ggcttgcatc gctgaacatc | 540 |
| gccattggga tttcttagaa agcagctctt gctcttatac aaacaccttc ctgcgtgcct | 600 |
| caccttactt acgaggagta atgttgtttt tacaggctag tggaactctt gcgcgcgagg | 660 |

```
ctgatcgagt ccggctggcg ggacgatctg aaggcattta caaaaggtac accactcggc    720
acttggcctg ttttgttgcc actagctacc aggccgtgac tgaccacgaa cccttcctct    780
ggagaataga aaggatccag tcccgggaga ctacaatgtc tgttgacgag gtcatcagag    840
aagtcggccc acatgctaga ggtaagcccc gcgagaacct tatatgctga ttagtgccat    900
ccgttgaaca tcgtctgatc tgcgacaagt tctggtaata cttgatagcc accgtcccag    960
acaaggtcaa gacagaactt cttgcgcaaa tcagtacttt tatcgaagac aacatgtaac   1020
gaaaaataaa aatgctgata tggaagggaa catcacgtac gccaggtacg tgagatgttt   1080
ttcctttttt ttttatttt  tttgttgggg cttgagatgt tttgggtctt tcatgaagac   1140
gttcatgaca aacaagaaat acggacagcg agtttaccgc aatggaaaag tttacctcaa   1200
ccgaactttg aacgttcgt  gaaaacctgc gtgagaattc tttgagcatg gccatacccta  1260 attgtcgccg gactgatctg tgatttgatc catggtccat cgctcctgac tcgctgcacg   1320
tcctgacaga gataacctcg catagtgtcg tacagaaacc aaaagcacgc gctcggtcca   1380
gtacagtaat ggggaactgg gtactgagga cagcttgaaa gtatatcctg taggggacga   1440
taacatgggc aatcttgatg gtgtggttga gtacagggta tatgcgttcc aggtaagcaa   1500
atatcacctt tgtgagacga taggggggcag ctatagtaaa tggccaggcg cttttatacg  1560
ggaagcaatt gcagcgatgg aggtgtgtac gctgcagccg cttgtatagc agaacgtaac   1620
cccaatcctc caactccggc aaggacaatg gggaagaag  gccggatata taaaatgctt   1680
gtcagcagaa ttaaagactg tgcggactga tctgccttaa tcggaaactt cagcagggct   1740
tctcgcagtg catgaaccct cggaccatct cctgtcccaa caacacgcca atgggcttat   1800
tattaatttt ttttggctgc cgttcaaaaa aaaaagaaa  aaaactgcca cttcttattt   1860
gagggctgca ggactgcttg ttaaggcgga taacctcaat ccgcccgatg ccttttaacg   1920
ctggcctgtt cttcctcttt tctttcttct ctcccttcac ccgtcttcac cctccctctt   1980 cccccgttc  ctacgtctac agccgttggc tcatcttgca gttgcttgtc tactatttgg   2040
tgccgaccta tattcctctg tcacccaacc taccgcactc acactcgcat aatggagtct   2100
ggacctatgc ctgccgggat ccccttccct gaatactatg acttttcat  ggactggaag   2160 acacccctgg caattgctgc cacctacacc gccgctgttg ggctcttcaa ccccaaggtt   2220
ggc                                                                 2223
```

<210> SEQ ID NO 18
<211> LENGTH: 3557
<212> TYPE: DNA
<213> ORGANISM: Mortierella alpina
<220> FEATURE:
<221> NAME/KEY: misc_feature
<222> LOCATION: (2092)..(2094)
<223> OTHER INFORMATION: ATG translation initiation codon
<220> FEATURE:
<221> NAME/KEY: misc_feature
<222> LOCATION: (2917)..(2919)
<223> OTHER INFORMATION: 'TAA' stop codon

<400> SEQUENCE: 18

```
actatagggc acgcgtggtc gacggcccgg gctggtccta cctctcaatc ttgttgccct     60
gtagtcctga aatgagctcg tcatgggtct ctgtcctctc ctcgttatgg tcaaacgcat    120
tggacccggt tttctttaga ggagcattct tcttgtttaa gccgactcct cttcccgtcc    180
cgaacgacaa cttgataggt ccaccatttc catttggtgg gtgaagcggg ctgtcctcag    240
cggacatgac tctgagctag aaggaagggt gtagaggacg aaggagtaag tgctaccgtt    300
```

-continued

```
cactggcagg tgaggagcgt cgggtctaag ccacatgcct gccaattgtc ctcgccaagt      360
gcttggaagg tgtattgatg ctcatgcagc tccactctgg acctggaaac gccaccgcat      420
cgcattctta atgagctctg ctacaaacga caatctgcga accagtttgc acagggagct      480
agtcgagtct ggaaagcggg accagtgagt gactcggcgg ggcttgcatc gctgaacatc      540
gccattggga tttcttagaa agcagctctt gctcttatac aaacaccttc ctgcgtgcct      600
caccttactt acgaggagta atgttgtttt tacaggctag tggaactctt gcgcgcgagg      660
ctgatcgagt ccggctggcg ggacgatctg aaggcattta caaaaggtac accactcggc      720
acttggcctg ttttgttgcc actagctacc aggccgtgac tgaccacgaa cccttcctct      780
ggagaataga aaggatccag tcccgggaga ctacaatgtc tgttgacgag gtcatcagag      840
aagtcggccc acatgctaga ggtaagcccc gcgagaacct tatatgctga ttagtgccat      900
ccgttgaaca tcgtctgatc tgcgacaagt tctggtaata cttgatagcc accgtcccag      960
acaaggtcaa gacagaactt cttgcgcaaa tcagtacttt tatcgaagac aacatgtaac     1020
gaaaaataaa aatgctgata tggaagggaa catcacgtac gccaggtacg tgagatgttt     1080 ttccttttt ttttattttt tttgttgggg cttgagatgt tttgggtctt tcatgaagac     1140
gttcatgaca acaagaaat acggacagcg agtttaccgc aatggaaaag tttacctcaa     1200
ccgaactttg aacgtttcgt gaaaacctgc gtgagaattc tttgagcatg gccataccta     1260
attgtcgccg gactgatctg tgatttgatc catggtccat cgctcctgac tcgctgcacg     1320
tcctgacaga gataaccctcg catagtgtcg tacagaaacc aaaagcacgc gctcggtcca     1380
gtacagtaat ggggaactgg gtactgagga cagcttgaaa gtatatcctg taggggacga     1440
taacatgggc aatcttgatg gtgtggttga gtacagggta tatgcgttcc aggtaagcaa     1500
atatcacctt tgtgagacga taggggggcag ctatagtaaa tggccaggcg ctttttatacg     1560 ggaagcaatt gcagcgatgg aggtgtgtac gctgcagccg cttgtatagc agaacgtaac     1620
cccaatcctc caactccggc aaggacaatg gggaagaag gccggatata taaaatgctt     1680
gtcagcagaa ttaaagactg tgcggactga tctgccttaa tcggaaactt cagcagggct     1740
tctcgcagtg catgaaccct cggaccatct cctgtcccaa caacacgcca atgggcttat     1800 tattaattt ttttggctgc cgttcaaaaa aaaaagaaa aaaactgcca cttcttattt     1860
gagggctgca ggactgcttg ttaaggcgga taacctcaat ccgcccgatg ccttttaacg     1920
ctggcctgtt cttcctcttt tctttcttct ctcccttcac ccgtcttcac cctccctctt     1980
ccccccgttc ctacgtctac agccgttggc tcatcttgca gttgcttgtc tactatttgg     2040
tgccgaccta tattcctctg tcacccaacc taccgcactc acactcgcat aatggagtct     2100
ggacctatgc ctgccgggat ccccttccct gaatactatg actttttcat ggactggaag     2160
acacccctgg caattgctgc cacctacacc gccgctgttg ggctcttcaa ccccaaggtt     2220
ggcaaagtct cgcgcgtggt agccaagtcg gctaacgcca agccggcaga gcgcacgcag     2280
tccggcgccg ccatgaccgc ctttgtcttt gtccacaacc ttatcctctg cgtgtactct     2340
ggaatcacct tctactacat gttcccagcc atggtcaaga actttagaac acatacccctc     2400 catgaggcct actgcgatac ggatcagagc ctgtggaaca acgcccttgg ctactggggc     2460
tacctcttct accttttcaaa gttttacgag gtcattgaca ccatcatcat catcttgaag     2520
gggcgccgct cgtccctgct ccagacctac caccacgccg gcgctatgat caccatgtgg     2580
tccggcatca actaccaggc aacgcccatt tggatttttg tcgtcttcaa ctcgttcatc     2640
```

```
cacaccatca tgtactgtta ctatgccttc acctcaatcg gcttccaccc cccaggcaag    2700
aagtacctca cctccatgca gatcacccag tttttggtcg gcatcactat cgccgtctct    2760
tatctcttcg tccctggatg tatccgcaca cccggtgctc agatggctgt ctggatcaac    2820
gtcggatacc tctttcccct cacttatctc tttgtggatt ttgccaagcg tacttactcc    2880
aagcgtagtg ccatcgccgc tcagaagaag gcccagtaaa gaggccactt cttgtcgttt    2940
actctactgt ttccaacatt tacatctctc aatggcagcc tcctccctct atccttcgca    3000 cttcattt agttccttgt attcataaaa rgtcaaaatt cattgtaact ccaaaagtgc       3060
caatggcttt atcatggatg agtgccatgt ttatggccca ttgcatcaat acaggaagat    3120
atgagcggtc agcgatagct attcctctga gttgtcctgg ccttgtatgc actctcgaag    3180
gaggaaatgg atcggagcat cagcactatt tcaggactag gagagataca tccaaaattt    3240
taaaggcatc tctggtcagt acaagagcga cttggcaaca agtctttagt caaacttcct    3300
cacctttgaa cttcctcaga ggtcgccgtg gcactgtgga cggagacccg tgaaaagaac    3360
tcatgcagca ggttaagcaa ccttggaaat ccatcgatga atgcctgatg taaaaattga    3420
gaagctgcaa gagccaaaag ttcagttcag cacatataag agactttggc caagagcgat    3480
gaagtcacat gggaaccacg taaacaaacc tcgtgcggag saccagcccg ggccgtcgac    3540
cacgcgtgcc ctatagt                                                   3557

<210> SEQ ID NO 19
<211> LENGTH: 542
<212> TYPE: DNA
<213> ORGANISM: Mortierella alpina
<220> FEATURE:
<221> NAME/KEY: Intron
<222> LOCATION: (1)..(542)

<400> SEQUENCE: 19
cgtaagttga caacggttca aatttcgaaa cttgcactgt gggtttgtcc tggttttatt      60
cggcagcttt tttctccgaa gtcttggccc agggaggagg caagaagagc aattcagggt     120
aggggcgtcc ggagattgga ccctgccttg gactagcgaa tggaatacga gagcgaagct     180
gtctgcatgg gctgatgata atatttttta ctggagatga ttgtaaggtg cggcgcgagg     240
gtgtagtaca tcagtcgaca tggattcaac caaatgttct ctagcagcga taaccctggc     300
tgtcttttgt taatcacggc aatgctatcc ccaaagaaaa aaaaagggt gcggttggca      360 cacggttgca caatggctta gccagacaat taacccaaaa aagtcaagag attccttttt     420
tttttttttt ttttttgggg ggggaacggg aaagtggggg ctgtgtgaaa ttgggggcgaa    480 gtgaaccatg caactttgag ctacaaacac ctaattgttt ttgtcttgcc tgacattatt    540
ag                                                                   542

<210> SEQ ID NO 20
<211> LENGTH: 6457
<212> TYPE: DNA
<213> ORGANISM: Artificial Sequence
<220> FEATURE:
<223> OTHER INFORMATION: Plasmid pKUNT2

<400> SEQUENCE: 20
tttgaatcga atcgatgagc taaaatgaa cccgagtata tctcataaaa ttctcggtga       60
gaggtctgtg actgtcagta caaggtgcct tcattatgcc ctcaacctta ccatacctca    120
ctgaatgtag tgtacctcta aaaatgaaat acagtgccaa aagccaaggc actgagctcg    180
```

-continued

| | |
|---|---|
| tctaacggac ttgatataca accaattaaa acaaatgaaa agaaatacag ttctttgtat | 240 |
| catttgtaac aattaccctg tacaaactaa ggtattgaaa tcccacaata ttcccaaagt | 300 |
| ccacccettt ccaaattgtc atgcctacaa ctcatatacc aagcactaac ctaccgttta | 360 |
| aacaccacta aacccaca aaatatatct taccgaatat acagatctgc gacgacggaa | 420 |
| ttcctgcagc ccatctgcag aattcaggag agaccgggtt ggcggcgtat ttgtgtccca | 480 |
| aaaaacagcc ccaattgccc caattgaccc caaattgacc cagtagcggg cccaaccccg | 540 |
| gcgagagccc ccttcacccc acatatcaaa cctcccccgg ttcccacact tgccgttaag | 600 |
| ggcgtagggt actgcagtct ggaatctacg cttgttcaga ctttgtacta gtttctttgt | 660 |
| ctggccatcc gggtaaccca tgccggacgc aaaatagact actgaaaatt tttttgcttt | 720 |
| gtggttggga ctttagccaa gggtataaaa gaccaccgtc cccgaattac ctttcctctt | 780 |
| cttttctctc tctccttgtc aactcacacc cgaaatcgtt aagcatttcc ttctgagtat | 840 |
| aagaatcatt caccatggat tcgaccacgc agaccaacac cggcaccggc aaggtggccg | 900 |
| tgcagccccc cacggccttc attaagccca ttgagaaggt gtccgagccc gtctacgaca | 960 |
| cctttggcaa cgagttcact cctccagact actctatcaa ggatattctg gatgccattc | 1020 |
| cccaggagtg ctacaagcgg tcctacgtta agtcctactc gtacgtggcc cgagactgct | 1080 |
| tctttatcgc cgttttttgcc tacatggcct acgcgtacct gcctcttatt ccctcggctt | 1140 |
| ccggccgagc tgtggcctgg gccatgtact ccattgtcca gggtctgttt ggcaccggtc | 1200 |
| tgtgggttct tgcccacgag tgtggccact ctgctttctc cgactctaac accgtcaaca | 1260 |
| acgtcaccgg atgggttctg cactcctcca tgctggtccc ttactacgcc tggaagctga | 1320 |
| cccactccat gcaccacaag tccactggtc acctcacccg tgatatggtg tttgtgccca | 1380 |
| aggaccgaaa ggagtttatg gagaaccgag gcgcccatga ctggtctgag cttgctgagg | 1440 |
| acgctcccct catgacectc tacgcctca tcacccagca ggtgtttgga tggcctctgt | 1500 |
| atctgctgtc ttacgttacc ggacagaagt accccaagct caacaaatgg gctgtcaacc | 1560 |
| acttcaaccc caacgccccg ctgtttgaga agaaggactg gttcaacatc tggatctcta | 1620 |
| acgtcggtat tggtatcacc atgtccgtca tcgcatactc catcaaccga tggggcctgg | 1680 |
| cttccgtcac cctctactac ctgatcccct acctgtgggt caaccactgg ctcgtggcca | 1740 |
| tcacctacct gcagcacacc gaccccactc tgccccacta ccacgccgac cagtggaact | 1800 |
| tcacccgagg agccgccgcc accatcgacc gagagtttgg cttcatcggc tccttctgct | 1860 |
| tccatgacat catcgagacc cacgttctgc accactacg gtctcgaatt cccttctaca | 1920 |
| acgcccgaat cgccactgag aagatcaaga aggtcatggg caagcactac cgacacgacg | 1980 |
| acaccaactt catcaagtct ctttacactg tcgcccgaac ctgccagttt gttgaaggta | 2040 |
| aggaaggcat tcagatgttt agaaacgtca atggagtcgg agttgctcct gacggcctgc | 2100 |
| cttctaaaaa gtaggcggcc gcaagtgtgg atggggaagt gagtgccgg ttctgtgtgc | 2160 |
| acaattggca atccaagatg gatggattca acacagggat atagcgagct acgtggtggt | 2220 |
| gcgaggatat agcaacggat atttatgttt gacacttgag aatgtacgat acaagcactg | 2280 |
| tccaagtaca atactaaaca tactgtacat actcatactc gtacccgggc aacggtttca | 2340 |
| cttgagtgca gtggctagtg ctcttactcg tacagtgtgc aatactgcgt atcatagtct | 2400 |
| ttgatgtata tcgtattcat tcatgttagt tgcgtacgaa gtcgtcaatg atgtcgatat | 2460 |
| gggttttgat catgcacaca taaggtccga cctatcggc aagctcaatg agctccttgg | 2520 |
| tggtggtaac atccagagaa gcacacaggt tggttttctt ggctgccacg agcttgagca | 2580 |

```
ctcgagcggc aaaggcggac ttgtggacgt tagctcgagc ttcgtaggag ggcattttgg    2640
tggtgaagag gagactgaaa taaatttagt ctgcagaact ttttatcgga accttatctg    2700
gggcagtgaa gtatatgtta tggtaatagt tacgagttag ttgaacttat agatagactg    2760
gactatacgg ctatcggtcc aaattagaaa gaacgtcaat ggctctctgg gcgtcgcctt    2820
tgccgacaaa aatgtgatca tgatgaaagc cagcaatgac gttgcagctg atattgttgt    2880
cggccaaccg cgccgaaaac gcagctgtca gacccacagc ctccaacgaa gaatgtatcg    2940
tcaaagtgat ccaagcacac tcatagttgg agtcgtactc caaaggcggc aatgacgagt    3000
cagacagata ctcgtcgacc ttttccttgg gaaccaccac cgtcagccct tctgactcac    3060
gtattgtagc caccgacaca ggcaacagtc cgtggatagc agaatatgtc ttgtcggtcc    3120
atttctcacc aactttaggc gtcaagtgaa tgttgcagaa gaagtatgtg ccttcattga    3180
gaatcggtgt tgctgatttc aataaagtct tgagatcagt ttggcgcgcc agctgcatta    3240
atgaatcggc caacgcgcgg ggagaggcgg tttgcgtatt gggcgctctt ccgcttcctc    3300
gctcactgac tcgctgcgct cggtcgttcg gctgcggcga cggtatcag ctcactcaaa    3360 ggcggtaata cggttatcca cagaatcagg ggataacgca ggaaagaaca tgtgagcaaa    3420
aggccagcaa aaggccagga accgtaaaaa ggccgcgttg ctggcgtttt tccataggct    3480
ccgcccccct gacgagcatc acaaaaatcg acgctcaagt cagaggtggc gaaacccgac    3540
aggactataa agataccagg cgtttccccc tggaagctcc ctcgtgcgct ctcctgttcc    3600
gaccctgccg cttaccggat acctgtccgc ctttctccct tcgggaagcg tggcgctttc    3660
tcatagctca cgctgtaggt atctcagttc ggtgtaggtc gttcgctcca agctgggctg    3720
tgtgcacgaa ccccccgttc agcccgaccg ctgcgcctta tccggtaact atcgtcttga    3780
gtccaacccg gtaagacacg acttatcgcc actggcagca gccactggta acaggattag    3840
cagagcgagg tatgtaggcg gtgctacaga gttcttgaag tggtggccta actacggcta    3900
cactagaaga acagtatttg gtatctgcgc tctgctgaag ccagttacct tcggaaaaag    3960
agttggtagc tcttgatccg gcaaacaaac caccgctggt agcggtggtt ttttgtttg    4020 caagcagcag attacgcgca gaaaaaaagg atctcaagaa gatcctttga tcttttctac    4080
ggggtctgac gctcagtgga acgaaaactc acgttaaggg attttggtca tgagattatc    4140
aaaaaggatc ttcacctaga tccttttaaa ttaaaaatga agttttaaat caatctaaag    4200
tatatatgag taaacttggt ctgacagtta ccaatgctta atcagtgagg cacctatctc    4260
agcgatctgt ctatttcgtt catccatagt tgcctgactc cccgtcgtgt agataactac    4320
gatacgggag ggcttaccat ctggccccag tgctgcaatg ataccgcgag acccacgctc    4380
accggctcca gatttatcag caataaacca gccagccgga agggccgagc gcagaagtgg    4440
tcctgcaact ttatccgcct ccatccagtc tattaattgt tgccgggaag ctagagtaag    4500
tagttcgcca gttaatagtt tgcgcaacgt tgttgccatt gctacaggca tcgtggtgtc    4560
acgctcgtcg tttggtatgg cttcattcag ctccggttcc caacgatcaa ggcgagttac    4620
atgatccccc atgttgtgca aaaaagcggt tagctccttc ggtcctccga tcgttgtcag    4680
aagtaagttg gccgcagtgt tatcactcat ggttatggca gcactgcata attctcttac    4740
tgtcatgcca tccgtaagat gcttttctgt gactggtgag tactcaacca agtcattctg    4800
agaatagtgt atgcggcgac cgagttgctc ttgcccggcg tcaatacggg ataataccgc    4860
gccacatagc agaactttaa aagtgctcat cattggaaaa cgttcttcgg ggcgaaaact    4920
```

-continued

```
ctcaaggatc ttaccgctgt tgagatccag ttcgatgtaa cccactcgtg cacccaactg    4980
atcttcagca tcttttactt tcaccagcgt ttctgggtga gcaaaaacag gaaggcaaaa    5040
tgccgcaaaa aagggaataa gggcgacacg gaaatgttga atactcatac tcttcctttt    5100
tcaatattat tgaagcattt atcagggtta ttgtctcatg agcggataca tatttgaatg    5160
tatttagaaa aataaacaaa taggggttcc gcgcacattt ccccgaaaag tgccacctga    5220
tgcggtgtga ataccgcac agatgcgtaa ggagaaaata ccgcatcagg aaattgtaag     5280
cgttaatatt tgttaaaat cgcgttaaa ttttgttaa atcagctcat tttttaacca       5340
ataggccgaa atcggcaaaa tcccttataa atcaaaagaa tagaccgaga tagggttgag    5400
tgttgttcca gtttggaaca agagtccact attaaagaac gtggactcca acgtcaaagg    5460
gcgaaaaacc gtctatcagg gcgatggccc actacgtgaa ccatcaccct aatcaagttt    5520
tttggggtcg aggtgccgta aagcactaaa tcggaaccct aaagggagcc cccgatttag    5580
agcttgacgg ggaaagccgg cgaacgtggc gagaaaggga gggaagaaag cgaaaggagc    5640
gggcgctagg gcgctggcaa gtgtagcggt cacgctgcgc gtaaccacca cacccgccgc    5700
gcttaatgcg ccgctacagg gcgcgtccat tcgccattca ggctgcgcaa ctgttgggaa    5760
gggcgatcgg tgcgggcctc ttcgctatta cgccagctgg cgaaagggg atgtgctgca    5820 aggcgattaa gttgggtaac gccagggttt tcccagtcac gacgttgtaa aacgacggcc    5880
agtgaattgt aatacgactc actatagggc gaattgggcc cgacgtcgca tgcagtggtg    5940
gtattgtgac tggggatgta gttgagaata agtcatacac aagtcagctt tcttcgagcc    6000
tcatataagt ataagtagtt caacgtatta gcactgtacc cagcatctcc gtatcgagaa    6060
acacaacaac atgccccatt ggacagatca tgcggataca caggttgtgc agtatcatac    6120
atactcgatc agacaggtcg tctgaccatc atacaagctg aacaagcgct ccatacttgc    6180
acgctctcta tatacacagt taaattacat atccatagtc taacctctaa cagttaatct    6240
tctggtaagc ctcccagcca gccttctggt atcgcttggc ctcctcaata ggatctcggt    6300
tctggccgta cagacctcgg ccgacaatta tgatatccgt tccggtagac atgcatcct    6360 caacagttcg gtactgctgt ccgagagcgt ctcccttgtc gtcaagaccc accccggggg    6420
tcagaataag ccagtcctca gagtcgccct taattaa                            6457
```

<210> SEQ ID NO 21
<211> LENGTH: 1936
<212> TYPE: DNA
<213> ORGANISM: Yarrowia lipolytica
<220> FEATURE:
<221> NAME/KEY: CDS
<222> LOCATION: (283)..(1539)
<223> OTHER INFORMATION: delta-12 desaturase

<400> SEQUENCE: 21

```
cgtagttata tacaagaggt agatgcgtgc tggtgttaga ggggctctca ggattaggag     60
gaaaatttga cattggccct caacatataa cctcgggtgt gcctctgttt accctcagct    120
tttgcttgtc cccaagtcag tcacgccagg ccaaaaaggt tggtggattg acagggagaa    180
aaaaaaaagc ctagtgggtt taaactcgag gtaagacatt gaaatatata ccggtcggca    240
tcctgagtcc ctttctcgta ttccaacaga ccgaccctag aa atg gat tcg acc       294
                                              Met Asp Ser Thr
                                              1 acg cag acc aac acc ggc acc ggc aag gtg gcc gtg cag ccc ccc acg     342
Thr Gln Thr Asn Thr Gly Thr Gly Lys Val Ala Val Gln Pro Pro Thr
 5                  10                  15                  20
```

-continued

```
gcc ttc att aag ccc att gag aag gtg tcc gag ccc gtc tac gac acc        390
Ala Phe Ile Lys Pro Ile Glu Lys Val Ser Glu Pro Val Tyr Asp Thr
            25                  30                  35 ttt ggc aac gag ttc act cct cca gac tac tct atc aag gat att ctg        438
Phe Gly Asn Glu Phe Thr Pro Pro Asp Tyr Ser Ile Lys Asp Ile Leu
        40                  45                  50 gat gcc att ccc cag gag tgc tac aag cgg tcc tac gtt aag tcc tac        486
Asp Ala Ile Pro Gln Glu Cys Tyr Lys Arg Ser Tyr Val Lys Ser Tyr
    55                  60                  65 tcg tac gtg gcc cga gac tgc ttc ttt atc gcc gtt ttt gcc tac atg        534
Ser Tyr Val Ala Arg Asp Cys Phe Phe Ile Ala Val Phe Ala Tyr Met
70                  75                  80 gcc tac gcg tac ctg cct ctt att ccc tcg gct tcc ggc cga gct gtg        582
Ala Tyr Ala Tyr Leu Pro Leu Ile Pro Ser Ala Ser Gly Arg Ala Val
85                  90                  95                 100 gcc tgg gcc atg tac tcc att gtc cag ggt ctg ttt ggc acc ggt ctg        630
Ala Trp Ala Met Tyr Ser Ile Val Gln Gly Leu Phe Gly Thr Gly Leu
                105                 110                 115 tgg gtt ctt gcc cac gag tgt ggc cac tct gct ttc tcc gac tct aac        678
Trp Val Leu Ala His Glu Cys Gly His Ser Ala Phe Ser Asp Ser Asn
            120                 125                 130 acc gtc aac aac gtc acc gga tgg gtt ctg cac tcc tcc atg ctg gtc        726
Thr Val Asn Asn Val Thr Gly Trp Val Leu His Ser Ser Met Leu Val
        135                 140                 145 cct tac tac gcc tgg aag ctg acc cac tcc atg cac cac aag tcc act        774
Pro Tyr Tyr Ala Trp Lys Leu Thr His Ser Met His His Lys Ser Thr
    150                 155                 160 ggt cac ctc acc cgt gat atg gtg ttt gtg ccc aag gac cga aag gag        822
Gly His Leu Thr Arg Asp Met Val Phe Val Pro Lys Asp Arg Lys Glu
165                 170                 175                 180 ttt atg gag aac cga ggc gcc cat gac tgg tct gag ctt gct gag gac        870
Phe Met Glu Asn Arg Gly Ala His Asp Trp Ser Glu Leu Ala Glu Asp
                185                 190                 195 gct ccc ctc atg acc ctc tac ggc ctc atc acc cag cag gtg ttt gga        918
Ala Pro Leu Met Thr Leu Tyr Gly Leu Ile Thr Gln Gln Val Phe Gly
            200                 205                 210 tgg cct ctg tat ctg ctg tct tac gtt acc gga cag aag tac ccc aag        966
Trp Pro Leu Tyr Leu Leu Ser Tyr Val Thr Gly Gln Lys Tyr Pro Lys
        215                 220                 225 ctc aac aaa tgg gct gtc aac cac ttc aac ccc aac gcc ccg ctg ttt       1014
Leu Asn Lys Trp Ala Val Asn His Phe Asn Pro Asn Ala Pro Leu Phe
    230                 235                 240 gag aag aag gac tgg ttc aac atc tgg atc tct aac gtc ggt att ggt       1062
Glu Lys Lys Asp Trp Phe Asn Ile Trp Ile Ser Asn Val Gly Ile Gly
245                 250                 255                 260 atc acc atg tcc gtc atc gca tac tcc atc aac cga tgg ggc ctg gct       1110
Ile Thr Met Ser Val Ile Ala Tyr Ser Ile Asn Arg Trp Gly Leu Ala
                265                 270                 275 tcc gtc acc ctc tac tac ctg atc ccc tac ctg tgg gtc aac cac tgg       1158
Ser Val Thr Leu Tyr Tyr Leu Ile Pro Tyr Leu Trp Val Asn His Trp
            280                 285                 290 ctc gtg gcc atc acc tac ctg cag cac acc gac ccc act ctg ccc cac       1206
Leu Val Ala Ile Thr Tyr Leu Gln His Thr Asp Pro Thr Leu Pro His
        295                 300                 305 tac cac gcc gac cag tgg aac ttc acc cga gga gcc gcc gcc acc atc       1254
Tyr His Ala Asp Gln Trp Asn Phe Thr Arg Gly Ala Ala Ala Thr Ile
    310                 315                 320 gac cga gag ttt ggc ttc atc ggc tcc ttc tgc ttc cat gac atc atc       1302
Asp Arg Glu Phe Gly Phe Ile Gly Ser Phe Cys Phe His Asp Ile Ile
```

-continued

```
                  325                 330                 335                 340
gag acc cac gtt ctg cac cac tac gtg tct cga att ccc ttc tac aac            1350
Glu Thr His Val Leu His His Tyr Val Ser Arg Ile Pro Phe Tyr Asn
                345                 350                 355 gcc cga atc gcc act gag aag atc aag aag gtc atg ggc aag cac tac            1398
Ala Arg Ile Ala Thr Glu Lys Ile Lys Lys Val Met Gly Lys His Tyr
            360                 365                 370 cga cac gac gac acc aac ttc atc aag tct ctt tac act gtc gcc cga            1446
Arg His Asp Asp Thr Asn Phe Ile Lys Ser Leu Tyr Thr Val Ala Arg
            375                 380                 385 acc tgc cag ttt gtt gaa ggt aag gaa ggc att cag atg ttt aga aac            1494
Thr Cys Gln Phe Val Glu Gly Lys Glu Gly Ile Gln Met Phe Arg Asn
        390                 395                 400 gtc aat gga gtc gga gtt gct cct gac ggc ctg cct tct aaa aag                1539
Val Asn Gly Val Gly Val Ala Pro Asp Gly Leu Pro Ser Lys Lys
405                 410                 415 tagagctaga aatgttattt gattgtgttt taactgaaca gcaccgagcc cgaggctaag          1599
ccaagcgaag ccgaggggtt gtgtagtcca tggacgtaac gagtaggcga tatcaccgca          1659
ctcggcactg cgtgtctgcg ttcatgggcg aagtcacatt acgctgacaa ccgttgtagt          1719
ttccctttag tatcaatact gttacaagta ccggtctcgt actcgtactg atacgaatct          1779
gtgggaagaa gtcacccctta tcagaccttc atactgatgt ttcggatatc aatagaactg         1839
gcatagagcc gttaaagaag tttcacttaa tcactccaac cctcctactt gtagattcaa          1899
gcagatcgat aagatggatt tgatggtcag tgctagc                                    1936
```

<210> SEQ ID NO 22
<211> LENGTH: 419
<212> TYPE: PRT
<213> ORGANISM: Yarrowia lipolytica

<400> SEQUENCE: 22

```
Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
            20                  25                  30

Val Tyr Asp Thr Phe Gly Asn Glu Phe Thr Pro Pro Asp Tyr Ser Ile
        35                  40                  45

Lys Asp Ile Leu Asp Ala Ile Pro Gln Glu Cys Tyr Lys Arg Ser Tyr
    50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
            100                 105                 110

Gly Thr Gly Leu Trp Val Leu Ala His Glu Cys Gly His Ser Ala Phe
        115                 120                 125

Ser Asp Ser Asn Thr Val Asn Asn Val Thr Gly Trp Val Leu His Ser
    130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
            180                 185                 190
```

Leu Ala Glu Asp Ala Pro Leu Met Thr Leu Tyr Gly Leu Ile Thr Gln
        195                 200                 205

Gln Val Phe Gly Trp Pro Leu Tyr Leu Ser Tyr Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
    290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys

<210> SEQ ID NO 23
<211> LENGTH: 24
<212> TYPE: DNA
<213> ORGANISM: Artificial Sequence
<220> FEATURE:
<223> OTHER INFORMATION: Primer MA ELONG 5' NcoI 3

<400> SEQUENCE: 23
gatcccatgg agtctggacc tatg                                    24

<210> SEQ ID NO 24
<211> LENGTH: 30
<212> TYPE: DNA
<213> ORGANISM: Artificial Sequence
<220> FEATURE:
<223> OTHER INFORMATION: Primer MA ELONG 3' NotI 1

<400> SEQUENCE: 24
gatcgcggcc gcttactggg ccttcttctg                              30

<210> SEQ ID NO 25
<211> LENGTH: 5553
<212> TYPE: DNA
<213> ORGANISM: Artificial Sequence
<220> FEATURE:
<223> OTHER INFORMATION: Plasmid pZF5T-PPC

<400> SEQUENCE: 25

```
ggccgcattg atgattggaa acacacacat gggttatatc taggtgagag ttagttggac    60
agttatatat taaatcagct atgccaacgg taacttcatt catgtcaacg aggaaccagt   120
gactgcaagt aatatagaat ttgaccacct tgccattctc ttgcactcct ttactatatc   180
tcatttattt cttatataca aatcacttct tcttcccagc atcgagctcg gaaacctcat   240
gagcaataac atcgtggatc tcgtcaatag agggcttttt ggactccttg ctgttggcca   300
ccttgtcctt gctgtctggc tcattctgtt tcaacgcctt ttaattaatc gagcttggcg   360
taatcatggt catagctgtt tcctgtgtga aattgttatc cgctcacaat tccacacaac   420
atacgagccg gaagcataaa gtgtaaagcc tggggtgcct aatgagtgag ctaactcaca   480
ttaattgcgt tgcgctcact gcccgctttc cagtcgggaa acctgtcgtg ccagctgcat   540
taatgaatcg gccaacgcgc ggggagaggc ggtttgcgta ttgggcgctc ttccgcttcc   600
tcgctcactg actcgctgcg ctcggtcgtt cggctgcggc gagcggtatc agctcactca   660
aaggcggtaa tacggttatc cacagaatca ggggataacg caggaaagaa catgtgagca   720
aaaggccagc aaaaggccag gaaccgtaaa aaggccgcgt tgctggcgtt tttccatagg   780
ctccgccccc ctgacgagca tcacaaaaat cgacgctcaa gtcagaggtg gcgaaacccg   840
acaggactat aaagatacca ggcgtttccc cctggaagct ccctcgtgcg ctctcctgtt   900
ccgaccctgc cgcttaccgg atacctgtcc gcctttctcc cttcgggaag cgtggcgctt   960
tctcatagct cacgctgtag gtatctcagt tcggtgtagg tcgttcgctc caagctgggc  1020
tgtgtgcacg aaccccccgt tcagcccgac cgctgcgcct tatccggtaa ctatcgtctt  1080
gagtccaacc cggtaagaca cgacttatcg ccactggcag cagccactgg taacaggatt  1140
agcagagcga ggtatgtagg cggtgctaca gagttcttga agtggtggcc taactacggc  1200
tacactagaa ggacagtatt tggtatctgc gctctgctga agccagttac cttcggaaaa  1260
agagttggta gctcttgatc cggcaaacaa accaccgctg gtagcggtgg tttttttgtt  1320
tgcaagcagc agattacgcg cagaaaaaaa ggatctcaag aagatccttt gatcttttct  1380
acggggtctg acgctcagtg gaacgaaaac tcacgttaag ggattttggt catgagatta  1440
tcaaaaagga tcttcaccta gatcctttta aattaaaaat gaagttttaa atcaatctaa  1500
agtatatatg agtaaacttg gtctgacagt taccaatgct taatcagtga ggcacctatc  1560
tcagcgatct gtctatttcg ttcatccata gttgcctgac tccccgtcgt gtagataact  1620
acgatacggg agggcttacc atctggcccc agtgctgcaa tgataccgcg agacccacgc  1680
tcaccggctc cagatttatc agcaataaac cagccagccg aagggccga gcgcagaagt  1740 ggtcctgcaa ctttatccgc ctccatccag tctattaatt gttgccggga agctagagta  1800
agtagttcgc cagttaatag tttgcgcaac gttgttgcca ttgctacagg catcgtggtg  1860
tcacgctcgt cgtttggtat ggcttcattc agctccggtt cccaacgatc aaggcgagtt  1920
acatgatccc ccatgttgtg caaaaaagcg gttagctcct tcggtcctcc gatcgttgtc  1980
agaagtaagt tggccgcagt gttatcactc atggttatgg cagcactgca taattctctt  2040
actgtcatgc catccgtaag atgcttttct gtgactggtg agtactcaac caagtcattc  2100
tgagaatagt gtatgcggcg accgagttgc tcttgcccgg cgtcaatacg gataatacc  2160 gcgccacata gcagaacttt aaaagtgctc atcattggaa aacgttcttc ggggcgaaaa  2220
ctctcaagga tcttaccgct gttgagatcc agttcgatgt aacccactcg tgcacccaac  2280
tgatcttcag catcttttac tttcaccagc gtttctgggt gagcaaaaac aggaaggcaa  2340
aatgccgcaa aaaagggaat aagggcgaca cggaaatgtt gaatactcat actcttcctt  2400
```

```
tttcaatatt attgaagcat ttatcagggt tattgtctca tgagcggata catatttgaa    2460
tgtatttaga aaaataaaca aataggggtt ccgcgcacat ttccccgaaa agtgccacct    2520
gacgcgccct gtagcggcgc attaagcgcg gcgggtgtgg tggttacgcg cagcgtgacc    2580
gctacacttg ccagcgccct agcgcccgct cctttcgctt tcttcccttc ctttctcgcc    2640
acgttcgccg gctttccccg tcaagctcta atcggggggc tccctttagg gttccgattt    2700
agtgctttac ggcacctcga ccccaaaaaa cttgattagg gtgatggttc acgtagtggg    2760
ccatcgccct gatagacggt ttttcgccct ttgacgttgg agtccacgtt ctttaatagt    2820
ggactcttgt tccaaactgg aacaacactc aaccctatct cggtctattc ttttgattta    2880
taagggattt tgccgatttc ggcctattgg ttaaaaaatg agctgattta acaaaaattt    2940
aacgcgaatt ttaacaaaat attaacgctt acaatttcca ttcgccattc aggctgcgca    3000
actgttggga agggcgatcg gtgcgggcct cttcgctatt acgccagctg gcgaaagggg    3060
gatgtgctgc aaggcgatta agttgggtaa cgccagggtt ttcccagtca cgacgttgta    3120
aaacgacggc cagtgaattg taatacgact cactataggg cgaattgggt accgggcccc    3180
ccctcgaggt cgacgtttaa acagtgtacg cagtactata gaggaacatc gattgccccg    3240
gagaagacgg ccaggccgcc tagatgacaa attcaacaac tcacagctga ctttctgcca    3300
ttgccactag ggggggggcct ttttatatgg ccaagccaag ctctccacgt cggttgggct    3360
gcacccaaca ataaatgggt agggttgcac caacaaaggg atgggatggg gggtagaaga    3420
tacgaggata acggggctca atggcacaaa taagaacgaa tactgccatt aagactcgtg    3480
atccagcgac tgacaccatt gcatcatcta agggcctcaa aactacctcg gaactgctgc    3540
gctgatctgg acaccacaga ggttccgagc actttaggtt gcaccaaatg tcccaccagg    3600
tgcaggcaga aaacgctgga acagcgtgta cagtttgtct taacaaaaag tgagggcgct    3660
gaggtcgagc agggtggtgt gacttgttat agcctttaga gctgcgaaag cgcgtatgga    3720
tttggctcat caggccagat tgagggtctg tggacacatg tcatgttagt gtacttcaat    3780
cgccccctgg atatagcccc gacaataggc cgtggcctca ttttttttgcc ttccgcacat    3840 ttccattgct cggtacccac accttgcttc tcctgcactt gccaacccta atactggttt    3900
acattgacca acatcttaca agcgggggggc ttgtctaggg tatatataaa cagtggctct    3960
cccaatcggt tgccagtctc ttttttttcctt tctttcccca cagattcgaa atctaaacta    4020
cacatcacac aatgcctgtt actgacgtcc ttaagcgaaa gtccggtgtc atcgtcggcg    4080
acgatgtccg agccgtgagt atccacgaca agatcagtgt cgagacgacg cgttttgtgt    4140
aatgacacaa tccgaaagtc gctagcaaca cacactctct acacaaacta acccagctct    4200
ccatgggaac ggaccaagga aaaaccttca cctgggaaga gctggcggcc cataacacca    4260
aggacgacct actcttggcc atccgcggca gggtgtacga tgtcacaaag ttcttgagcc    4320
gccatcctgg tggagtggac actctcctgc tcggagctgg ccgagatgtt actccggtct    4380
ttgagatgta tcacgcgttt ggggctgcag atgccattat gaagaagtac tatgtcggta    4440
cactggtctc gaatgagctg cccatcttcc cggagccaac ggtgttccac aaaaccatca    4500
agacgagagt cgagggctac tttacggatc ggaacattga tcccaagaat agaccagaga    4560
tctggggacg atacgctctt atctttggat ccttgatcgc ttcctactac gcgcagctct    4620
ttgtgccttt cgttgtcgaa cgcacatggc ttcaggtggt gtttgcaatc atcatgggat    4680
ttgcgtgcgc acaagtcgga ctcaaccctc ttcatgatgc gtctcacttt tcagtgaccc    4740
```

```
acaaccccac tgtctggaag attctgggag ccacgcacga cttttttcaac ggagcatcgt    4800 acctggtgtg gatgtaccaa catatgctcg gccatcaccc ctacaccaac attgctggag    4860
cagatcccga cgtgtcgacg tctgagcccg atgttcgtcg tatcaagccc aaccaaaagt    4920
ggtttgtcaa ccacatcaac cagcacatgt ttgttccttt cctgtacgga ctgctggcgt    4980
tcaaggtgcg cattcaggac atcaacattt tgtactttgt caagaccaat gacgctattc    5040
gtgtcaatcc catctcgaca tggcacactg tgatgttctg gggcggcaag gctttctttg    5100
tctggtatcg cctgattgtt ccctgcagt atctgcccct gggcaaggtg ctgctcttgt    5160
tcacggtcgc ggacatggtg tcgtcttact ggctggcgct gaccttccag gcgaaccacg    5220
ttgttgagga agttcagtgg ccgttgcctg acgagaacgg gatcatccaa aaggactggg    5280
cagctatgca ggtcgagact acgcaggatt acgcacacga ttcgcacctc tggaccagca    5340
tcactggcag cttgaactac caggctgtgc accatctgtt ccccaacgtg tcgcagcacc    5400
attatcccga tattctggcc atcatcaaga acacctgcag cgagtacaag gttccatacc    5460
ttgtcaagga tacgttttgg caagcatttg cttcacattt ggagcacttg cgtgttcttg    5520
gactccgtcc caaggaagag taggcagcta agc                                5553

<210> SEQ ID NO 26
<211> LENGTH: 5031
<212> TYPE: DNA
<213> ORGANISM: Artificial Sequence
<220> FEATURE:
<223> OTHER INFORMATION: Plasmid pZF5T-PPC-E3

<400> SEQUENCE: 26
atggagtctg gacctatgcc tgccgggatc cccttccctg aatactatga cttttttcatg      60 gactggaaga caccccctggc aattgctgcc acctacaccg ccgctgttgg gctcttcaac     120
cccaaggttg gcaaagtctc gcgcgtggta gccaagtcgg ctaacgccaa gccggcagag     180
cgcacgcagt ccggcgccgc catgaccgcc tttgtctttg tccacaacct tatcctctgc     240
gtgtactctg gaatcacctt ctactacatg ttcccagcca tggtcaagaa ctttagaaca     300
cataccctcc atgaggccta ctgcgatacg gatcagagcc tgtggaacaa cgcccttggc     360
tactggggct acctcttcta cctttcaaag ttttacgagg tcattgacac catcatcatc     420
atcttgaagg ggcgccgctc gtccctgctc cagacctacc accacgccgg cgctatgatc     480
accatgtggt ccggcatcaa ctaccaggca acgcccattt ggattttttgt cgtcttcaac     540 tcgttcatcc acaccatcat gtactgttac tatgccttca cctcaatcgg cttccacccc     600
ccargcaaga agtacctcac ctccatgcag atcacccagt ttttggtcgg catcactatc     660
gccgtctctt atctcttcgt ccctggatgt atccgcacac ccggtgctca gatggctgtc     720
tggatcaacg tcggatacct cttttcccctc acttatctct tgtggatttt tgccaagcgt    780
acttactcca gcgtagtgc catcgccgct cagaagaagg cccagtaagg ccgcattgat     840
gattggaaac acacacatgg ttatatctga ggtgagagtt agttggacag ttatatatta     900
aatcagctat gccaacggta acttcattca tgtcaacgag gaaccagtga ctgcaagtaa     960
tatagaattt gaccaccttg ccattctctt gcactccttt actatatctc atttatttct    1020
tatatacaaa tcacttcttc ttcccagcat cgagctcgga aacctcatga gcaataacat    1080
cgtggatctc gtcaatagag ggcttttttgg actccttgct gttggccacc ttgtccttgc    1140
tgtctggctc attctgtttc aacgcctttt aattaatcga gcttggcgta atcatggtca    1200
tagctgtttc ctgtgtgaaa ttgttatccg ctcacaattc cacacaacat acgagccgga    1260
```

```
agcataaagt gtaaagcctg gggtgcctaa tgagtgagct aactcacatt aattgcgttg   1320
cgctcactgc ccgctttcca gtcgggaaac ctgtcgtgcc agctgcatta atgaatcggc   1380
caacgcgcgg ggagaggcgg tttgcgtatt gggcgctctt ccgcttcctc gctcactgac   1440
tcgctgcgct cggtcgttcg gctgcggcga gcggtatcag ctcactcaaa ggcggtaata   1500
cggttatcca cagaatcagg ggataacgca ggaaagaaca tgtgagcaaa aggccagcaa   1560
aaggccagga accgtaaaaa ggccgcgttg ctggcgtttt tccataggct ccgcccccct   1620
gacgagcatc acaaaaatcg acgctcaagt cagaggtggc gaaacccgac aggactataa   1680
agataccagg cgtttccccc tggaagctcc ctcgtgcgct ctcctgttcc gaccctgccg   1740
cttaccggat acctgtccgc ctttctccct tcgggaagcg tggcgctttc tcatagctca   1800
cgctgtaggt atctcagttc ggtgtaggtc gttcgctcca agctgggctg tgtgcacgaa   1860
ccccccgttc agcccgaccg ctgcgcctta tccggtaact atcgtcttga gtccaacccg   1920
gtaagacacg acttatcgcc actggcagca gccactggta acaggattag cagagcgagg   1980
tatgtaggcg gtgctacaga gttcttgaag tggtggccta actacggcta cactagaagg   2040
acagtatttg gtatctgcgc tctgctgaag ccagttacct tcggaaaaag agttggtagc   2100
tcttgatccg gcaaacaaac caccgctggt agcggtggtt ttttttgttt gcaagcagca   2160
attacgcgca gaaaaaaagg atctcaagaa gatcctttga tcttttctac ggggtctgac   2220
gctcagtgga acgaaaactc acgttaaggg attttggtca tgagattatc aaaaaggatc   2280
ttcacctaga tccttttaaa ttaaaaatga agttttaaat caatctaaag tatatatgag   2340
taaacttggt ctgacagtta ccaatgctta atcagtgagg cacctatctc agcgatctgt   2400
ctatttcgtt catccatagt tgcctgactc cccgtcgtgt agataactac gatacgggag   2460
ggcttaccat ctggccccag tgctgcaatg ataccgcgag acccacgctc accggctcca   2520
gatttatcag caataaacca gccagccgga agggccgagc gcagaagtgg tcctgcaact   2580
ttatccgcct ccatccagtc tattaattgt tgccgggaag ctagagtaag tagttcgcca   2640
gttaatagtt tgcgcaacgt tgttgccatt gctacaggca tcgtggtgtc acgctcgtcg   2700
tttggtatgg cttcattcag ctccggttcc caacgatcaa ggcgagttac atgatccccc   2760
atgttgtgca aaaaagcggt tagctccttc ggtcctccga tcgttgtcag aagtaagttg   2820
gccgcagtgt tatcactcat ggttatggca gcactgcata attctcttac tgtcatgcca   2880
tccgtaagat gcttttctgt gactggtgag tactcaacca agtcattctg agaatagtgt   2940
atgcggcgac cgagttgctc ttgcccggcg tcaatacggg ataataccgc gccacatagc   3000
agaactttaa aagtgctcat cattggaaaa cgttcttcgg ggcgaaaact ctcaaggatc   3060
ttaccgctgt tgagatccag ttcgatgtaa cccactcgtg cacccaactg atcttcagca   3120
tcttttactt tcaccagcgt ttctgggtga gcaaaaacag gaaggcaaaa tgccgcaaaa   3180
aagggaataa gggcgacacg gaaatgttga atactcatac tcttcctttt tcaatattat   3240
tgaagcattt atcagggtta ttgtctcatg agcggataca tatttgaatg tatttagaaa   3300
aataaacaaa taggggttcc gcgcacattt ccccgaaaag tgccacctga cgcgccctgt   3360
agcggcgcat taagcgcggc gggtgtggtg gttacgcgca gcgtgaccgc tacacttgcc   3420
agcgccctag cgcccgctcc tttcgctttc ttcccttcct ttctcgccac gttcgccggc   3480
tttccccgtc aagctctaaa tcgggggctc cctttagggt tccgatttag tgctttacgg   3540
cacctcgacc ccaaaaaact tgattagggt gatggttcac gtagtgggcc atcgccctga   3600
```

```
tagacggttt ttcgcccttt gacgttggag tccacgttct ttaatagtgg actcttgttc    3660
caaactggaa caacactcaa ccctatctcg gtctattctt ttgatttata agggattttg    3720
ccgatttcgg cctattggtt aaaaaatgag ctgatttaac aaaaatttaa cgcgaatttt    3780
aacaaaatat taacgcttac aatttccatt cgccattcag gctgcgcaac tgttgggaag    3840
ggcgatcggt gcgggcctct tcgctattac gccagctggc gaaaggggga tgtgctgcaa    3900
ggcgattaag ttgggtaacg ccagggtttt cccagtcacg acgttgtaaa acgacggcca    3960
gtgaattgta atacgactca ctatagggcg aattgggtac cgggcccccc ctcgaggtcg    4020
acgtttaaac agtgtacgca gtactataga ggaacatcga ttgccccgga gaagacggcc    4080
aggccgccta gatgacaaat tcaacaactc acagctgact ttctgccatt gccactaggg    4140
gggggccttt ttatatggcc aagccaagct ctccacgtcg gttgggctgc acccaacaat    4200
aaatgggtag ggttgcacca acaaagggat gggatggggg gtagaagata cgaggataac    4260
ggggctcaat ggcacaaata gaacgaata ctgccattaa gactcgtgat ccagcgactg    4320
acaccattgc atcatctaag ggcctcaaaa ctacctcgga actgctgcgc tgatctggac    4380
accacagagt tccgagcac tttaggttgc accaaatgtc ccaccaggtg caggcagaaa    4440
acgctggaac agcgtgtaca gtttgtctta acaaaaagtg agggcgctga ggtcgagcag    4500
ggtggtgtga cttgttatag cctttagagc tgcgaaagcg cgtatggatt tggctcatca    4560
ggccagattg agggtctgtg gacacatgtc atgttagtgt acttcaatcg ccccctggat    4620
atagccccga caataggccg tggcctcatt tttttgcctt ccgcacattt ccattgctcg    4680
gtacccacac cttgcttctc ctgcacttgc caaccttaat actggtttac attgaccaac    4740
atcttacaag cgggggggctt gtctagggta tatataaaca gtggctctcc caatcggttg    4800
ccagtctctt ttttccttc ttccccaca gattcgaaat ctaaactaca catcacacaa    4860
tgcctgttac tgacgtcctt aagcgaaagt ccggtgtcat cgtcggcgac gatgtccgag    4920
ccgtgagtat ccacgacaag atcagtgtcg agacgacgcg ttttgtgtaa tgacacaatc    4980
cgaaagtcgc tagcaacaca cactctctac acaaactaac ccagctctcc a              5031
```

<210> SEQ ID NO 27
<211> LENGTH: 8462
<212> TYPE: DNA
<213> ORGANISM: Artificial Sequence
<220> FEATURE:
<223> OTHER INFORMATION: Plasmid pZUF6S

<400> SEQUENCE: 27

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc ggcaacggtt tcacttgag tgcagtggct     240 agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta ttgcgttgc gctcactgcc cgctttccag tcgggaaacc     420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag gccgcgttgc     660
```

-continued

```
tggcgttttt ccataggctc cgccccctg acgagcatca caaaaatcga cgctcaagtc      720
agaggtggcg aaacccgaca ggactataaa gataccaggc gtttccccct ggaagctccc      780
tcgtgcgctc tcctgttccg accctgccgc ttaccggata cctgtccgcc tttctccctt      840
cgggaagcgt ggcgctttct catagctcac gctgtaggta tctcagttcg gtgtaggtcg      900
ttcgctccaa gctgggctgt gtgcacgaac ccccgttca gcccgaccgc tgcgccttat       960
ccggtaacta tcgtcttgag tccaacccgg taagacacga cttatcgcca ctggcagcag     1020
ccactggtaa caggattagc agagcgaggt atgtaggcgg tgctacagag ttcttgaagt     1080
ggtggcctaa ctacggctac actagaagga cagtatttgg tatctgcgct ctgctgaagc     1140
cagttacctt cggaaaaaga gttggtagct cttgatccgg caaacaaacc accgctggta     1200
gcggtggttt ttttgtttgc aagcagcaga ttacgcgcag aaaaaaagga tctcaagaag     1260
atcctttgat cttttctacg gggtctgacg ctcagtggaa cgaaaactca cgttaaggga     1320
ttttggtcat gagattatca aaaggatctt cacctagat cctttttaaat taaaaatgaa     1380
gttttaaatc aatctaaagt atatatgagt aaacttggtc tgacagttac caatgcttaa     1440
tcagtgaggc acctatctca gcgatctgtc tatttcgttc atccatagtt gcctgactcc     1500
ccgtcgtgta gataactacg atacgggagg gcttaccatc tggccccagt gctgcaatga     1560
taccgcgaga cccacgctca ccggctccag atttatcagc aataaaccag ccagccggaa     1620
gggccgagcg cagaagtggt cctgcaactt tatccgcctc catccagtct attaattgtt     1680
gccgggaagc tagagtaagt agttcgccag ttaatagttt cgcaacgtt gttgccattg     1740
ctacaggcat cgtggtgtca cgctcgtcgt ttggtatggc ttcattcagc tccggttccc     1800
aacgatcaag gcgagttaca tgatccccca tgttgtgcaa aaaagcggtt agctccttcg     1860
gtcctccgat cgttgtcaga agtaagttgg ccgcagtgtt atcactcatg gttatggcag     1920
cactgcataa ttctcttact gtcatgccat ccgtaagatg cttttctgtg actggtgagt     1980
actcaaccaa gtcattctga gaatagtgta tgcggcgacc gagttgctct tgcccggcgt     2040
caatacggga taataccgcg ccacatagca gaactttaaa agtgctcatc attggaaaac     2100
gttcttcggg gcgaaaactc tcaaggatct taccgctgtt gagatccagt tcgatgtaac     2160
ccactcgtgc acccaactga tcttcagcat cttttacttt caccagcgtt tctgggtgag     2220
caaaaacagg aaggcaaaat gccgcaaaaa agggaataag ggcgacacgg aaatgttgaa     2280
tactcatact cttccttttt caatattatt gaagcattta tcagggttat tgtctcatga     2340
gcggatacat atttgaatgt atttagaaaa ataaacaaat aggggttccg cgcacatttc     2400
cccgaaaagt gccacctgac gcgccctgta gcggcgcatt aagcgcggcg ggtgtggtgg     2460
ttacgcgcag cgtgaccgct acacttgcca gcgccctagc gcccgctcct ttcgctttct     2520
tcccttcctt tctcgccacg ttcgccggct ttccccgtca gctctaaat cggggctcc      2580
ctttagggtt ccgatttagt gctttacggc acctcgaccc caaaaaactt gattagggtg     2640
atggttcacg tagtgggcca tcgccctgat agacggtttt tcgccctttg acgttggagt     2700
ccacgttctt taatagtgga ctcttgttcc aaactggaac aacactcaac cctatctcgg     2760
tctattcttt tgatttataa gggattttgc cgatttcggc ctattggtta aaaaatgagc     2820
tgatttaaca aaaatttaac gcgaatttta caaaatatt aacgcttaca atttccattc      2880
gccattcagg ctgcgcaact gttgggaagg gcgatcggtg cgggcctctt cgctattacg     2940
ccagctggcg aaagggggat gtgctgcaag gcgattaagt tgggtaacgc cagggttttc     3000
```

```
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaagggt catctcgcat    3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc ccctcgttc agtgtcaact    4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
ttttttttt  ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg ctcccttgt cgtcaagacc cacccgggg    4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
```

```
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc aacgaagaa     5940
tgtatcgtca aagtgatcca agcacactca tagttggagt cgtactccaa aggcggcaat    6000
gacgagtcag acagatactc gtcgactcag gcgacgacgg aattcctgca gcccatctgc    6060
agaattcagg agagaccggg ttggcggcgt atttgtgtcc caaaaaacag ccccaattgc    6120
cccggagaag acggccaggc cgcctagatg acaaattcaa caactcacag ctgactttct    6180
gccattgcca ctaggggggg gccttttat atggccaagc caagctctcc acgtcggttg     6240
ggctgcaccc aacaataaat gggtagggtt gcaccaacaa agggatggga tgggggtag     6300
aagatacgag gataacgggg ctcaatggca caaataagaa cgaatactgc cattaagact    6360
cgtgatccag cgactgacac cattgcatca tctaagggcc tcaaaactac ctcggaactg    6420
ctgcgctgat ctggacacca cagaggttcc gagcacttta ggttgcacca aatgtcccac    6480
caggtgcagg cagaaaacgc tggaacagcg tgtacagttt gtcttaacaa aaagtgaggg    6540
cgctgaggtc gagcagggtg gtgtgacttg ttatagcctt tagagctgcg aaagcgcgta    6600
tggatttggc tcatcaggcc agattgaggg tctgtggaca catgtcatgt tagtgtactt    6660
caatcgcccc ctggatatag ccccgacaat aggccgtggc ctcattttt tgccttccgc     6720
acatttccat tgctcggtac ccacaccttg cttctcctgc acttgccaac cttaatactg    6780
gtttacattg accaacatct tacaagcggg gggcttgtct agggtatata taaacagtgg    6840
ctctcccaat cggttgccag tctcttttt cctttctttc cccacagatt cgaaatctaa     6900
actacacatc acacaatgcc tgttactgac gtccttaagc gaaagtccgg tgtcatcgtc    6960
ggcgacgatg tccgagccgt gagtatccac gacaagatca gtgtcgagac gacgcgtttt    7020
gtgtaatgac acaatccgaa agtcgctagc aacacacact ctctacacaa actaacccag    7080
ctctccatgg ctgccgctcc ctctgtgcga acctttaccc gagccgaggt tctgaacgct    7140
gaggctctga acgagggcaa gaaggacgct gaggctccct tcctgatgat catcgacaac    7200
aaggtgtacg acgtccgaga gttcgtccct gaccatcctg gaggctccgt gattctcacc    7260
cacgttggca aggacggcac cgacgtcttt gacacctttc atcccgaggc tgcttgggag    7320
actctcgcca acttctacgt tggagacatt gacgagtccg accgagacat caagaacgat    7380
gactttgccg ctgaggtccg aaagctgcga accctgttcc agtctctcgg ctactacgac    7440
tcctctaagg cctactacgc cttcaaggtc tccttcaacc tctgcatctg ggactgtcc     7500
accgtcattg tggccaagtg gggtcagacc tccaccctcg ccaacgtgct ctctgctgcc    7560
ctgctcggcc tgttctggca gcagtgcgga tggctggctc acgactttct gcaccaccag    7620
gtcttccagg accgattctg gggtgatctc ttcggagcct tcctgggagg tgtctgccag    7680
ggcttctcct cttcctggtg gaaggacaag cacaacactc accatgccgc tcccaacgtg    7740
```

```
catggcgagg atcctgacat tgacacccac cctctcctga cctggtccga gcacgctctg    7800
gagatgttct ccgacgtccc cgatgaggag ctgacccgaa tgtggtctcg attcatggtc    7860
ctgaaccaga cctggttcta cttccccatt ctctccttcg ctcgactgtc ttggtgcctc    7920
cagtccattc tctttgtgct gcccaacggt caggctcaca agccctccgg agctcgagtg    7980
cccatctccc tggtcgagca gctgtccctc gccatgcact ggacctggta cctcgctacc    8040
atgttcctgt tcatcaagga tcctgtcaac atgctcgtgt acttcctggt gtctcaggct    8100
gtgtgcggaa acctgctcgc catcgtgttc tccctcaacc acaacggtat gcctgtgatc    8160
tccaaggagg aggctgtcga catggatttc tttaccaagc agatcatcac tggtcgagat    8220
gtccatcctg gactgttcgc caactggttc accggtggcc tgaactacca gatcgagcat    8280
cacctgttcc cttccatgcc ctcgacacaa cttctccaaga tccagcctgc cgtcgagacc    8340
ctgtgcaaga agtacaacgt ccgataccac accactggta tgatcgaggg aactgccgag    8400
gtcttctccc gactgaacga ggtctccaag gccacctcca agatgggcaa ggctcagtaa    8460
gc                                                                    8462
```

<210> SEQ ID NO 28
<211> LENGTH: 11046
<212> TYPE: DNA
<213> ORGANISM: Artificial Sequence
<220> FEATURE:
<223> OTHER INFORMATION: Plasmid pZUF6S-E3WT

<400> SEQUENCE: 28

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta attgcgttgc gctcactgcc cgctttccag tcgggaaacc     420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag gccgcgttgc     660
tggcgttttt ccataggctc cgcccccctg acgagcatca caaaaatcga cgctcaagtc     720
agaggtggcg aaacccgaca ggactataaa gataccaggc gtttccccct ggaagctccc     780
tcgtgcgctc tcctgttccg accctgccgc ttaccggata cctgtccgcc tttctccctt     840
cgggaagcgt ggcgctttct catagctcac gctgtaggta tctcagttcg gtgtaggtcg     900
ttcgctccaa gctgggctgt gtgcacgaac cccccgttca gcccgaccgc tgcgccttat     960
ccggtaacta tcgtcttgag tccaacccgg taagacacga cttatcgcca ctggcagcag    1020
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
gcggtggttt ttttgtttgc aagcagcaga ttacgcgcag aaaaaaagga tctcaagaag    1260
atcctttgat cttttctacg gggtctgacg ctcagtggaa cgaaaactca cgttaaggga    1320
```

-continued

```
ttttggtcat gagattatca aaaaggatct tcacctagat cctttaaat taaaaatgaa    1380
gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg gcttaccatc tggccccagt gctgcaatga    1560
taccgcgaga cccacgctca ccggctccag atttatcagc aataaaccag ccagccggaa    1620
gggccgagcg cagaagtggt cctgcaactt tatccgcctc catccagtct attaattgtt    1680
gccgggaagc tagagtaagt agttcgccag ttaatagttt cgcaacgtt gttgccattg    1740
ctacaggcat cgtggtgtca cgctcgtcgt ttggtatggc ttcattcagc tccggttccc    1800
aacgatcaag gcgagttaca tgatccccca tgttgtgcaa aaaagcggtt agctccttcg    1860
gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga aatagtgta tgcggcgacc gagttgctct tgcccggcgt     2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttccttttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgccctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca gctctaaat cgggggctcc     2580
ctttagggtt ccgatttagt gctttacggc acctcgaccc caaaaaactt gattagggtg    2640
atggttcacg tagtgggcca tcgccctgat agacggtttt tcgcccttg acgttggagt     2700
ccacgttctt taatagtgga ctcttgttcc aaactggaac aacactcaac cctatctcgg    2760
tctattcttt tgatttataa gggattttgc cgatttcggc ctattggtta aaaaatgagc    2820
tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaagggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaagggt catctcgcat     3360
tgtttaataa taaacagact ccatctaccg cctccaaatg atgttctcaa aatatattgt    3420
atgaacttat ttttattact tagtattatt agacaactta cttgctttat gaaaacact     3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
```

```
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat ttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg ttttttttg    4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatgcagaat tcaggagaga ccgggttggc ggcgtatttg tgtcccaaaa   4560
aacagcccca attgccccaa ttgacccccaa attgacccag tagcgggccc aaccccggcg   4620
agagcccct tcaccccaca tatcaaacct cccccggttc ccacacttgc cgttaagggc   4680
gtagggtact gcagtctgga atctacgctt gttcagactt tgtactagtt tctttgtctg   4740
gccatccggg taacccatgc cggacgcaaa atagactact gaaaatttt ttgctttgtg   4800
gttgggactt tagccaaggg tataaaagac caccgtcccc gaattacctt tcctcttctt   4860
ttctctctct ccttgtcaac tcacacccga aatcgttaag catttccttc tgagtataag   4920
aatcattcac caggagagac cgggttggcg gcgtatttgt gtcccaaaaa acagccccaa   4980
ttgccccgga gaagacggcc aggccgccta gatgacaaat tcaacaactc acagctgact   5040
ttctgccatt gccactaggg gggggccttt ttatatggcc aagccaagct ctccacgtcg   5100
gttgggctgc acccaacaat aaatgggtag ggttgcacca acaaagggat gggatggggg   5160
gtagaagata cgaggataac ggggctcaat ggcacaaata agaacgaata ctgccattaa   5220
gactcgtgat ccagcgactg acaccattgc atcatctaag ggcctcaaaa ctacctcgga   5280
actgctcgcg tgatctggac accacagagg ttccgagcac tttaggttgc accaaatgtc   5340
ccaccaggtg caggcagaaa acgctggaac agcgtgtaca gtttgtctta acaaaaagtg   5400
agggcgctga ggtcgagcag ggtggtgtga cttgttatag cctttagagc tgcgaaagcg   5460
cgtatggatt tggctcatca ggccagattg agggtctgtg gacacatgtc atgttagtgt   5520
acttcaatcg ccccctggat atagccccga caataggccg tggcctcatt ttttgcctt    5580
ccgcacattt ccattgctcg gtacccacac cttgcttctc ctgcacttgc caaccttaat   5640
actggtttac attgaccaac atcttacaag cgggggggctt gtctaggta tatataaaca   5700
gtggctctcc caatcggttg ccagtctctt ttttcctttc tttccccaca gattcgaaat   5760
ctaaactaca catcacacaa tgcctgttac tgacgtcctt aagcgaaagt ccggtgtcat   5820
cgtcggcgac gatgtccgag ccgtgagtat ccacgacaag atcagtgtcg agacgacgcg   5880
ttttgtgtaa tgacacaatc cgaaagtcgc tagcaacaca cactctctac acaaactaac   5940
ccagctatgg agtctggacc tatgcctgcc gggatcccct tccctgaata ctatgacttt   6000
ttcatggact ggaagacacc cctggcaatt gctgccacct acaccgccgc tgttgggctc   6060
```

```
ttcaacccca aggttggcaa agtctcgcgc gtggtagcca agtcggctaa cgccaagccg      6120
gcagagcgca cgcagtccgg cgccgccatg accgcctttg tctttgtcca aaccttatc      6180 ctctgcgtgt actctggaat caccttctac tacatgttcc cagccatggt caagaacttt      6240
agaacacata ccctccatga ggcctactgc gatacggatc agagcctgtg aacaacgcc      6300 cttggctact ggggctacct cttctacctt tcaaagtttt acgaggtcat tgacaccatc      6360
atcatcatct tgaaggggcg ccgctcgtcc ctgctccaga cctaccacca cgccggcgct      6420
atgatcacca tgtggtccgg catcaactac caggcaacgc ccatttggat ttttgtcgtc      6480
ttcaactcgt tcatccacac catcatgtac tgttactatg ccttcacctc aatcggcttc      6540 cacccccar gcaagaagta cctcacctcc atgcagatca cccagttttt ggtcggcatc      6600
actatcgccg tctcttatct cttcgtccct ggatgtatcc gcacacccgg tgctcagatg      6660
gctgtctgga tcaacgtcgg atacctcttt cccctcactt atctctttgt ggattttgcc      6720
aagcgtactt actccaagcg tagtgccatc gccgctcaga agaaggccca gtaaattgat      6780
gattggaaac acacacatgg ttatatcta ggtgagagtt agttggacag ttatatatta      6840
aatcagctat gccaacggta acttcattca tgtcaacgag gaaccagtga ctgcaagtaa      6900
tatagaattt gaccaccttg ccattctctt gcactccttt actatatctc atttatttct      6960
tatatacaaa tcacttcttc ttcccagcat cgagctcgga aacctcatga gcaataacat      7020
cgtggatctc gtcaatagag ggcttttttgg actccttgct gttggccacc ttgtccttgc      7080
tgtctggctc attctgtttc aacgcctttt aattaagtca tacacaagtc agctttcttc      7140
gagcctcata taagtataag tagttcaacg tattagcact gtaccagca tctccgtatc      7200 gagaaacaca acaacatgcc ccattggaca gatcatgcgg atacacaggt tgtgcagtat      7260
catacatact cgatcagaca ggtcgtctga ccatcataca agctgaacaa gcgctccata      7320
cttgcacgct ctctatatac acagttaaat tacatatcca tagtctaacc tctaacagtt      7380
aatcttctgg taagcctccc agccagcctt ctggtatcgc ttggcctcct caataggatc      7440
tcggttctgg ccgtacagac ctcggccgac aattatgata tccgttccgg tagacatgac      7500
atcctcaaca gttcggtact gctgtccgag agcgtctccc ttgtcgtcaa gacccacccc      7560
gggggtcaga ataagccagt cctcagagtc gcccttaggt cggttctggg caatgaagcc      7620
aaccacaaac tcggggtcgg atcgggcaag ctcaatggtc tgcttggagt actcgccagt      7680
ggccagagag cccttgcaag acagctcggc cagcatgagc agacctctgg ccagcttctc      7740
gttgggagag gggactagga actccttgta ctgggagttc tcgtagtcag agacgtcctc      7800
cttcttctgt tcagagacag tttcctcggc accagctcgc aggccagcaa tgattccggt      7860
tccgggtaca ccgtgggcgt tggtgatatc ggaccactcg gcgattcggt gacaccggta      7920
ctggtgcttg acagtgttgc caatatctgc gaactttctg tcctcgaaca ggaagaaacc      7980
gtgcttaaga gcaagttcct tgaggggag cacagtgccg gcgtaggtga agtcgtcaat      8040
gatgtcgata tgggttttga tcatgcacac ataaggtccg accttatcgg caagctcaat      8100
gagctccttg gtggtggtaa catccagaga agcacacagg ttggttttct tggctgccac      8160
gagcttgagc actcgagcgg caaaggcgga cttgtggacg ttagctcgag cttcgtagga      8220
gggcattttg gtggtgaaga ggagactgaa ataaatttag tctgcagaac tttttatcgg      8280
aaccttatct ggggcagtga agtatatgtt atggtaatag ttacgagtta gttgaactta      8340
tagatagact ggactatacg gctatcggtc caaattagaa agaacgtcaa tggctctctg      8400
```

```
ggcgtcgcct tgccgacaa aaatgtgatc atgatgaaag ccagcaatga cgttgcagct   8460
gatattgttg tcggccaacc gcgccgaaaa cgcagctgtc agacccacag cctccaacga   8520
agaatgtatc gtcaaagtga tccaagcaca ctcatagttg gagtcgtact ccaaaggcgg   8580
caatgacgag tcagacagat actcgtcgac tcaggcgacg acggaattcc tgcagcccat   8640
ctgcagaatt caggagagac cgggttggcg gcgtatttgt gtcccaaaaa acagccccaa   8700
ttgccccgga gaagacggcc aggccgccta gatgacaaat tcaacaactc acagctgact   8760
ttctgccatt gccactaggg gggggccttt ttatatggcc aagccaagct ctccacgtcg   8820
gttgggctgc acccaacaat aaatgggtag ggttgcacca acaaagggat gggatggggg   8880
gtagaagata cgaggataac ggggctcaat ggcacaaata agaacgaata ctgccattaa   8940
gactcgtgat ccagcgactg acaccattgc atcatctaag ggcctcaaaa ctacctcgga   9000
actgctgcgc tgatctggac accacagagg ttccgagcac tttaggttgc accaaatgtc   9060
ccaccaggtg caggcagaaa acgctggaac agcgtgtaca gtttgtctta acaaaaagtg   9120
agggcgctga ggtcgagcag ggtggtgtga cttgttatag cctttagagc tgcgaaagcg   9180
cgtatggatt tggctcatca ggccagattg agggtctgtg gacacatgtc atgttagtgt   9240
acttcaatcg ccccctggat atagccccga caataggccg tggcctcatt ttttgccctt    9300
ccgcacattt ccattgctcg gtacccacac cttgcttctc ctgcacttgc caacttaat    9360 actggtttac attgaccaac atcttacaag cgggggcctt gtctaggta tatataaaca    9420 gtggctctcc caatcggttg ccagtctctt ttttcctttc tttcccaca gattcgaaat    9480 ctaaactaca catcacacaa tgcctgttac tgacgtcctt aagcgaaagt ccggtgtcat    9540
cgtcggcgac gatgtccgag ccgtgagtat ccacgacaag atcagtgtcg agacgacgcg    9600
ttttgtgtaa tgacacaatc cgaaagtcgc tagcaacaca cactctctac acaaactaac    9660
ccagctctcc atggctgccg ctccctctgt gcgaaccttt acccgagccg aggttctgaa    9720
cgctgaggct ctgaacgagg gcaagaagga cgctgaggct cccttcctga tgatcatcga    9780
caacaaggtg tacgacgtcc gagagttcgt ccctgaccat cctggaggct ccgtgattct    9840
cacccacgtt ggcaaggacg gcaccgacgt cttttgacacc tttcatcccg aggctgcttg    9900
ggagactctc gccaacttct acgttggaga cattgacgag tccgaccgag acatcaagaa    9960
cgatgacttt gccgctgagg tccgaaagct gcgaaccctg ttccagtctc tcggctacta   10020
cgactcctct aaggcctact acgccttcaa ggtctccttc aacctctgca tctgggact    10080 gtccaccgtc attgtggcca agtggggtca gacctccacc ctcgccaacg tgctctctgc   10140
tgccctgctc ggcctgttct ggcagcagtg cggatggctg gctcacgact ttctgcacca   10200
ccaggtcttc caggaccgat tctggggtga tctcttcgga gccttcctgg aggtgtctg    10260 ccagggcttc tcctcttcct ggtggaagga caagcacaac actcaccatg ccgctcccaa   10320
cgtgcatggc gaggatcctg acattgacac ccaccctctc ctgacctggt ccgagcacgc   10380
tctggagatg ttctccgacg tccccgatga ggagctgacc cgaatgtggt ctcgattcat   10440
ggtcctgaac cagacctggt tctacttccc cattctctcc ttcgctcgac tgtcttggtg   10500
cctccagtcc attctcttg tgctgcccaa cggtcaggct cacaagccct ccggagctcg   10560 agtgccatc tccctggtcg agcagctgtc cctcgccatg cactgaccct ggtacctcgc   10620
taccatgttc ctgttcatca aggatcctgt caacatgctc gtgtacttcc tggtgtctca   10680
ggctgtgtgg ggaaacctgc tcgccatcgt gttctccctc aaccacaacg gtatgcctgt   10740
gatctccaag gaggaggctg tcgacatgga tttctttacc aagcagatca tcactggtcg   10800
```

| | |
|---|---:|
| agatgtccat cctggactgt tcgccaactg gttcaccggt ggcctgaact accagatcga | 10860 |
| gcatcacctg ttcccttcca tgcctcgaca caacttctcc aagatccagc ctgccgtcga | 10920 |
| gaccctgtgc aagaagtaca acgtccgata ccacaccact ggtatgatcg agggaactgc | 10980 |
| cgaggtcttc tcccgactga acgaggtctc caaggccacc tccaagatgg gcaaggctca | 11040 |
| gtaagc | 11046 |

```
<210> SEQ ID NO 29
<211> LENGTH: 4099
<212> TYPE: DNA
<213> ORGANISM: Mortierella alpina
<220> FEATURE:
<221> NAME/KEY: misc_feature
<222> LOCATION: (2092)..(2094)
<223> OTHER INFORMATION: ATG translation initiation codon
<220> FEATURE:
<221> NAME/KEY: Intron
<222> LOCATION: (2410)..(2951)
<220> FEATURE:
<221> NAME/KEY: misc_feature
<222> LOCATION: (3459)..(3461)
<223> OTHER INFORMATION: 'TAA' stop codon

<400> SEQUENCE: 29
```

| | |
|---|---:|
| actatagggc acgcgtggtc gacggcccgg gctggtccta cctctcaatc ttgttgccct | 60 |
| gtagtcctga aatgagctcg tcatgggtct ctgtcctctc ctcgttatgg tcaaacgcat | 120 |
| tggacccggt tttctttaga ggagcattct tcttgtttaa gccgactcct cttcccgtcc | 180 |
| cgaacgacaa cttgataggt ccaccatttc catttggtgg gtgaagcggg ctgtcctcag | 240 |
| cggacatgac tctgagctag aaggaagggt gtagaggacg aaggagtaag tgctaccgtt | 300 |
| cactggcagg tgaggagcgt cgggtctaag ccacatgcct gccaattgtc ctcgccaagt | 360 |
| gcttggaagg tgtattgatg ctcatgcagc tccactctgg acctgaaaac gccaccgcat | 420 |
| cgcattctta atgagctctg ctacaaacga caatctgcga accagtttgc acagggagct | 480 |
| agtcgagtct ggaaagcggg accagtgagt gactcggcgg gcttgcatc gctgaacatc | 540 |
| gccattggga tttcttagaa agcagctctt gctcttatac aaacaccttc ctgcgtgcct | 600 |
| caccttactt acgaggagta atgttgtttt tacaggctag tggaactctt gcgcgcgagg | 660 |
| ctgatcgagt ccggctggcg ggacgatctg aaggcattta caaaaggtac accactcggc | 720 |
| acttggcctg ttttgttgcc actagctacc aggccgtgac tgaccacgaa cccttcctct | 780 |
| ggagaataga aaggatccag tcccgggaga ctacaatgtc tgttgacgag gtcatcagag | 840 |
| aagtcggccc acatgctaga ggtaagcccc gcgagaacct tatatgctga ttagtgccat | 900 |
| ccgttgaaca tcgtctgatc tgcgacaagt tctggtaata cttgatagcc accgtcccag | 960 |
| acaaggtcaa gacagaactt cttgcgcaaa tcagtacttt tatcgaagac aacatgtaac | 1020 |
| gaaaaataaa aatgctgata tggaagggaa catcacgtac gccaggtacg tgagatgttt | 1080 |
| ttcctttttt ttttatttt tttgttgggg cttgagatgt tttgggtctt tcatgaagac | 1140 |
| gttcatgaca aacaagaaat acggacagcg agtttaccgc aatggaaaag tttacctcaa | 1200 |
| ccgaactttg aacgtttcgt gaaaacctgc gtgagaattc tttgagcatg ccataccta | 1260 |
| attgtcgccg gactgatctg tgatttgatc catggtccat cgctcctgac tcgctgcacg | 1320 |
| tcctgacaga gataaccctcg catagtgtcg tacagaaacc aaaagcacgc gctcggtcca | 1380 |
| gtacagtaat ggggaactgg gtactgagga cagcttgaaa gtatatcctg taggggacga | 1440 |
| taacatgggc aatcttgatg gtgtggttga gtacagggta tatgcgttcc aggtaagcaa | 1500 |

-continued

```
atatcacctt tgtgagacga tagggggcag ctatagtaaa tggccaggcg ctttttatacg   1560 ggaagcaatt gcagcgatgg aggtgtgtac gctgcagccg cttgtatagc agaacgtaac   1620
cccaatcctc caactccggc aaggacaatg gggaaagaag gccggatata taaaatgctt   1680
gtcagcagaa ttaaagactg tgcggactga tctgccttaa tcggaaactt cagcagggct   1740
tctcgcagtg catgaaccct cggaccatct cctgtcccaa caacacgcca atgggcttat   1800
tattaatttt ttttggctgc cgttcaaaaa aaaaagaaa aaaactgcca cttcttattt   1860
gagggctgca ggactgcttg ttaaggcgga taacctcaat ccgcccgatg ccttttaacg   1920
ctggcctgtt cttcctcttt tctttcttct ctcccttcac ccgtcttcac cctccctctt   1980 cccccgttc ctacgtctac agccgttggc tcatcttgca gttgcttgtc tactatttgg   2040
tgccgaccta tattcctctg tcacccaacc taccgcactc acactcgcat aatggagtct   2100
ggacctatgc ctgccgggat ccccttccct gaatactatg acttttcat ggactggaag   2160 acacccctgg caattgctgc cacctacacc gccgctgttg ggctcttcaa ccccaaggtt   2220
ggcaaagtct cgcgcgtggt agccaagtcg gctaacgcca agccggcaga gcgcacgcag   2280
tccggcgccg ccatgaccgc ctttgtcttt gtccacaacc ttatcctctg cgtgtactct   2340
ggaatcacct tctactacat gttcccagcc atggtcaaga actttagaac acataccctc   2400
catgaggccc gtaagttgac aacggttcaa atttcgaaac ttgcactgtg ggtttgtcct   2460
ggttttattc ggcagctttt ttctccgaag tcttggccca gggaggaggc aagaagagca   2520
attcagggta ggggcgtccg gagattggac cctgccttgg actagcgaat ggaatacgag   2580
agcgaagctg tctgcatggg ctgatgataa tatttttac tggagatgat tgtaaggtgc   2640
ggcgcgaggg tgtagtacat cagtcgacat ggattcaacc aaatgttctc tagcagcgat   2700
aaccctggct gtcttttgtt aatcacggca atgctatccc caagaaaaa aaaaagggtg   2760 cggttggcac acggttgcac aatggcttag ccagacaatt aacccaaaaa agtcaagaga   2820 ttccttttt tttttttttt ttttgggg gggaacggga agtgggggc tgtgtgaaat   2880 tggggcgaag tgaaccatgc aactttgagc tacaaacacc taattgtttt tgtcttgcct   2940
gacattatta gtactgcgat acggatcaga gcctgtggaa caacgccctt ggctactggg   3000
gctacctctt ctacctttca aagttttacg aggtcattga caccatcatc atcatcttga   3060
aggggcgccg ctcgtccctg ctccagacct accaccacgc cggcgctatg atcaccatgt   3120
ggtccggcat caactaccag gcaacgccca tttggatttt tgtcgtcttc aactcgttca   3180
tccacaccat catgtactgt tactatgcct tcacctcaat cggcttccac cccccaggca   3240
agaagtacct cacctccatg cagatcaccc agttttggt cggcatcact atcgccgtct   3300
cttatctctt cgtccctgga tgtatccgca cacccggtgc tcagatggct gtctggatca   3360
acgtcggata cctcttcccc ctcacttatc tctttgtgga ttttgccaag cgtacttact   3420
ccaagcgtag tgccatcgcc gctcagaaga aggcccagta aagaggccac ttcttgtcgt   3480
ttactctact gtttccaaca tttacatctc tcaatggcag cctcctccct ctatccttcg   3540
cactttcatt ttagttcctt gtattcataa aargtcaaaa ttcattgtaa ctccaaaagt   3600
gccaatggct ttatcatgga tgagtgccat gtttatggcc cattgcatca atacaggaag   3660
atatgagcgg tcagcgatag ctattcctct gagttgtcct ggccttgtat gcactctcga   3720
aggaggaaat ggatcggagc atcagcacta tttcaggact aggagagata catccaaaat   3780
tttaaaggca tctctggtca gtacaagagc gacttggcaa caagtcttta gtcaaacttc   3840
```

```
ctcacctttg aacttcctca gaggtcgccg tggcactgtg gacggagacc cgtgaaaaga    3900
actcatgcag caggttaagc aaccttggaa atccatcgat gaatgcctga tgtaaaaatt    3960
gagaagctgc aagagccaaa agttcagttc agcacatata agagactttg gccaagagcg    4020
atgaagtcac atgggaacca cgtaaacaaa cctcgtgcgg agsaccagcc cgggccgtcg    4080
accacgcgtg ccctatagt                                                 4099
```